United States Patent
Elliott

(10) Patent No.: US 7,081,523 B2
(45) Date of Patent: *Jul. 25, 2006

(54) ANTIBODIES WHICH ACTIVATE AN ERYTHROPOIETIN RECEPTOR

(75) Inventor: Steven Elliott, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/364,276

(22) Filed: Feb. 10, 2003

(65) Prior Publication Data

US 2003/0215444 A1 Nov. 20, 2003

Related U.S. Application Data

(60) Continuation of application No. 09/640,090, filed on Aug. 17, 2000, now abandoned, which is a division of application No. 09/092,671, filed on Jun. 5, 1998, now abandoned, which is a division of application No. 08/280,864, filed on Jul. 26, 1994, now Pat. No. 5,885,574.

(51) Int. Cl.
- C12P 21/08 (2006.01)
- C07K 16/00 (2006.01)
- C07K 16/28 (2006.01)

(52) U.S. Cl. ............... 530/388.1; 530/388.15; 530/388.2; 530/388.22; 530/391.3

(58) Field of Classification Search ........... 530/387.1, 530/387.9, 388.1, 388.15, 388.2, 391.3, 388.22
See application file for complete search history.

(56) References Cited

U.S. PATENT DOCUMENTS

| | | | |
|---|---|---|---|
| 4,667,016 A | 5/1987 | Lai et al. |
| 4,703,008 A | 10/1987 | Lin |
| 4,816,567 A | 3/1989 | Cabilly et al. |
| 5,225,539 A | 7/1993 | Winter |
| 5,278,065 A | 1/1994 | D'Andrea et al. |
| 5,545,806 A | 8/1996 | Lonberg et al. |
| 5,736,137 A | 4/1998 | Anderson et al. |
| 5,885,574 A | 3/1999 | Elliott |
| 6,103,879 A | 8/2000 | Chaovapong et al. |

FOREIGN PATENT DOCUMENTS

| WO | WO 90/08822 | 8/1990 |
|---|---|---|
| WO | WO 92/21029 | 11/1992 |
| WO | WO 93/12227 | 6/1993 |

OTHER PUBLICATIONS

Cunningham et al. TIBTECH 10: 112-113, 1992.*
Anagnostou et al., *Proc. Nat. Acad. Sci. USA*, 91:3974-3978 (1994).
Bailey et al., *Exp. Hematol.*, 21:1535-1543 (1993).
Baynes et al., *Blood*, 82:2088-2095 (1993).
Broudy et al., *Proc. Nat. Acad. Sci. USA*, 85:6513 (1988).
Chiba et al., *Nature*, 362:646 (1993).
Chiba et al., *Proc. Natl. Acad. Sci. USA*, 90:11593 (1993).
D'Andrea et al., *Cell*, 57:277 (1989).
D'Andrea et al., *J. Cell Biochem.*, Suppl. 13 Part C: 25 (1989).
D'Andrea et al., *Blood*, 75:874-880 (1990).
D'Andrea et al., *The Biology of Hemtaopoiesis*, Wiley-Liss, Inc., pp. 153-159 (1990).
D'Andrea et al., *Blood*, 82:46-52 (1993).
DeClerck et al., *J. Biol. Chem.*, 266:3893 (1991).
Dong & Goldwasser, *Exp. Hematol.*, 21:483 (1993).
Eschbach et al., *N. Engl. J. Med.*, 316:73 (1987).
Fiagerstam et al., *J. Mol. Recognition*, 3:208 (1990).
Fisher et al., *Blood*, 82:197A (1993).
Fisher et al., *Blood*, 84:1982-1991 (1994).
Fuh et al., *Science*, 256:1677 (1992).
Harlow et al., Eds., "Antibodies: A Laboratory Manual," Cold Springs Harbor, NY, Chapter 9 (1988).
Harris et al., *J. Biol. Chem.*, 267:15205 (1992).
Hunt et al., *Exp. Hematol.*, 19:779 (1991).
Iscove et. al., *J. Cell. Physiol*, 83:309 (1974).
Jones et al., *Blood*, 76:31 (1990).
Komatsu et al., *Blood*, 82:456 (1993).
Koury, *Science*, 248:378 (1990).
Laemmli et al., *Nature*, 227:680 (1970).
Ledbetter et al., *Advanced Drug Delivery Reviews*, 2:319-342 (1988).
Liboi et al., *Proc. Natl. Acad. Sci. USA*, 90:11351 (1993).
Ludwig, H. et al., *New Eng. J. Med.*, 322(24):1693-1699 (1990).
Malmbory et al., *Scand. J. Immunol.*, 35:643 (1992).
Mayeux et al., *Eur. J. Biochem.*, 194:271 (1990).
Mayeux et al., *J. Biol. Chem.*, 266:23380 (1991).
McCaffery et al., *J. Biol. Chem.*, 264:10507 (1991).
Miura & Ihle, *Arch. Biochem. Biophys.*, 306:200 (1993).
Miura & Ihle, *Blood*, 81:1739 (1993).
Miyake et al., *J. Biol. Chem.* 252:5558 (1977).
Ngo et al., "The Protein Folding Problem and Tertiary Structure Prediction," K. Merz Jr. and S. Le Grand, Editors, Birkhauser Boston, pp. 492-495 (1994).
Noguchi et al., *Mol. Cell. Biol.*, 8:2604 (1988).
Patel et al., *J. Biol. Chem.*, 267:21300 (1992).

(Continued)

Primary Examiner—Christina Chan
Assistant Examiner—Marianne DiBrino
(74) Attorney, Agent, or Firm—Finnegan, Henderson, Farabow, Garrett & Dunner, LLP

(57) ABSTRACT

Antibodies and fragments thereof which activate an erythropoietin receptor and stimulate erythropoiesis are described. Also described are hybridoma cell lines which produce the antibodies and methods and compositions for the treatment of anemia.

17 Claims, 8 Drawing Sheets

OTHER PUBLICATIONS

Pharr et al., *Proc. Natl. Acad. Sci. USA*, 90:938 (1993).
Reichmann et al., "Reshaping human antibodies for therapy," *Nature*, 332:323-327 (1988).
Sawyer, *J. Biol. Chem.*, 264:13343 (1989).
Schreiber et al., *Proc. Natl. Acad. Sci. USA*, 78:7535 (1981).
Wigler et al., *Cell*, 11:223 (1977).
Winkelmann et al., *Blood*, 76:24 (1990).
Yet & Jones, *Blood*, 82:1713 (1993).
Xiong et al., *Proc. Natl. Acad. Sci. USA*, 89(12):5356-5360 (1992).
Yoshimura et al., *Nature*, 348:647 (1990).

* cited by examiner

FIG. 7
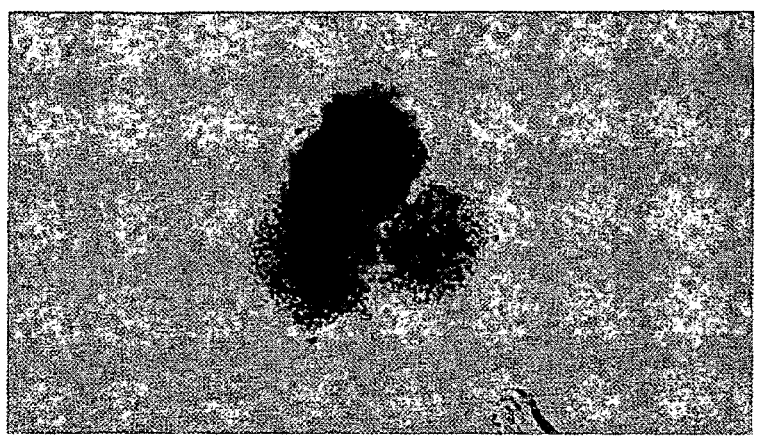
A
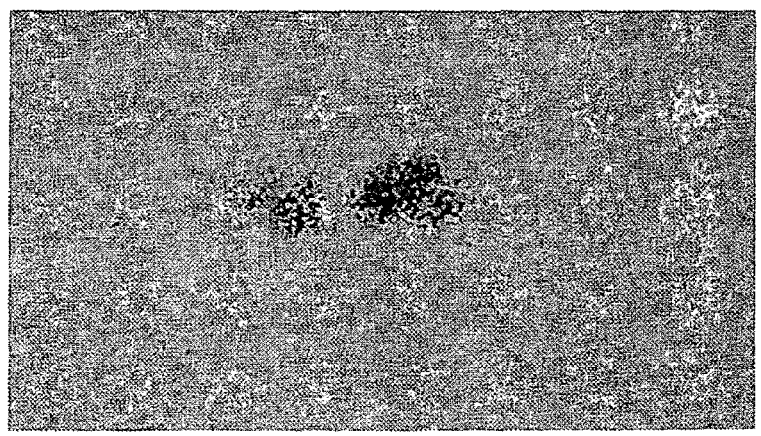
B
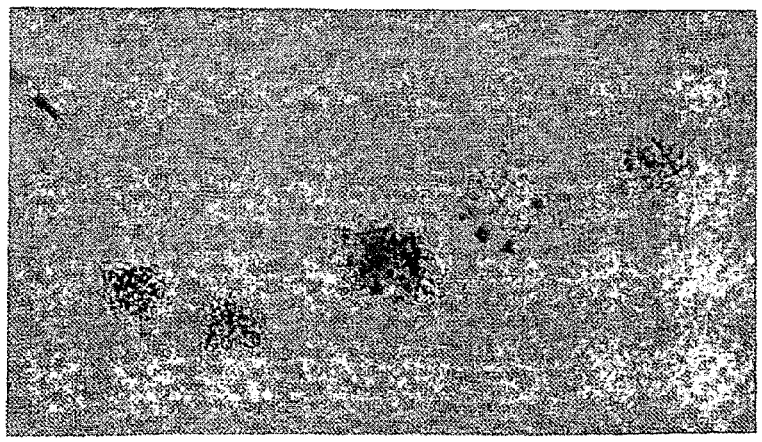
C

ANTIBODIES WHICH ACTIVATE AN ERYTHROPOIETIN RECEPTOR

This application is a continuation of U.S. application Ser. No. 09/640,090 filed Aug. 17, 2000, now abandoned, which is a divisional of U.S. application Ser. No. 09/092,671, filed June 5,1998, now abandoned, which is a divisional of U.S. application Ser. No. 08/280,864, filed Jul. 26, 1994, now U.S. Pat. No. 5,885,574.

FIELD OF THE INVENTION

This invention relates to antibodies which recognize an erythropoietin receptor. More particularly, the invention relates to antibodies which activate an erythropoietin receptor and stimulate erythropoiesis.

BACKGROUND OF THE INVENTION

Erythropoietin (EPO) is a glycoprotein hormone involved in the growth and maturation of erythroid progenitor cells into erythrocytes. EPO is produced by the liver during fetal life and by the kidney of adults and stimulates the production of red blood cells from erythroid precursors. Decreased production of EPO, which commonly occurs in adults as a result of renal failure, leads to anemia. EPO has been produced by genetic engineering techniques involving expression and secretion of the protein from a host cell transfected with the gene encoding erythropoietin. Administration of recombinant EPO has been effective in the treatment of anemia. For example, Eschbach et al. (N. Engl J Med 316, 73 (1987)) describe the use of EPO to correct anemia resulting from chronic renal failure.

The purification of human urinary EPO was described by Miyake et al. (J. Biol. Chem. 252, 5558 (1977)). The identification, cloning, and expression of genes encoding erythropoietin is described in U.S. Pat. No. 4,703,008 to Lin. A description of a method for purification of recombinant EPO from cell medium is included in U.S. Pat. No. 4,667,016 to Lai et al.

Little is known about the mechanism by which EPO stimulates erythropoiesis. While it is clear that EPO activates cells to grow and/or differentiate by binding to specific cell surface receptors, the specific mechanism of activation as well as the structure of the receptor and any associated protein(s) is not completely understood. The erythropoietin receptor (EPO-R) is thought to exist as a multimeric complex. Sedimentation studies suggested its molecular weight is 330±48 kDa (Mayeux et al. Eur. J. Biochem. 1, 271 (1990)). Crosslinking studies indicated that the receptor complex consists of at least two distinct polypeptides, a 66–72 kDa species, and 85 and 100 kDa species (Mayeux et al. J. Biol. Chem. 266, 23380 (1991)); McCaffery et al. J. Biol. Chem. 264, 10507 (1991)). A distinct 95 kDa protein was also detected by immunoprecipitation of EPO receptor (Miura & Ihle Blood 81, 1739 (1993)). Another crosslinking study revealed three EPO containing complexes of 110, 130 and 145 kDa. The 110 and 145 kDa complexes contained EPO receptor since they could be immunoprecipitated with antibodies raised against the receptor (Miura & Ihle, supra). Expression of a carboxy-terminal truncated EPO receptor resulted in detection of the 110 kDa complex but not the 145 kDa complex. This suggests that the higher molecular weight complex contains polypeptides present in the 110 kDa complex and an additional 35 kDa protein.

Further insight into the structure and function of the EPO receptor complex was obtained upon cloning and expression of the mouse and human EPO receptors (D'Andrea et al. Cell 57, 277 (1989); Jones et al. Blood 76, 31 (1990); Winkelmann et al. Blood 76, 24 (1990); PCT Application No. WO90/08822; U.S. Pat. No. 5,278,065 to D'Andrea et al.) The full-length human EPO receptor is a 483 amino acid transmembrane protein with an approximately 224 amino acid extracellular domain and a 25 amino acid signal peptide. The human receptor shows about an 82% amino acid sequence homology with tha mouse receptor. The cloned full length EPO receptor expressed in mammalian cells (66–72 KDa) has been shown to bind EPO with an affinity (100–300 nM) similar to that of the native receptor on erythroid progenitor cells. Thus this form is thought to contain the main EPO binding determinant and is referred to as the EPO receptor. The 85 and 100 KDa proteins observed as part of a cross-linked complex are distinct from the EPO receptor but must be in close proximity to EPO because EPO can be crosslinked to them. The 85 and 100 KDa proteins are related to each other and the 85 KDa protein may be a proteolytic cleavage product of the 100 KDa species (Sawyer J. Biol. Chem. 264, 13343 (1989)).

A soluble (truncated) form of the EPO receptor containing only the extracellular domain has been produced and found to bind EPO with an affinity of about 1 nM, or about 3 to 10-fold lower than the full-length receptor (Harris et al. J. Biol. Chem. 267, 15205 (1992); Yang & Jones Blood 82, 1713 (1993)). The reason for the reduced affinity as compared to the full length protein is not known. There is a possibility that other protein species may also be part of the EPOR complex and contribute to EPO binding thus increasing the affinity. In support of this possibility is the observation of Dong & Goldwasser (Exp. Hematol. 21, 483 (1993)) that fusion of a cell line with a low affinity EPO receptor with a CHO cell which does not bind EPO resulted in a hybrid cell line exhibiting high EPO binding affinity of the receptor for EPO. In addition, transfection of a full length EPOR into CHO cells resulted in a cell line with both high and low affinity receptors as measured by Scatchard analysis. Amplification of the EPOR copy number increased the low affinity but not high affinity binding. These results are consistent with the presence of a limited quantity of a protein present in CHO cells that converts the low affinity EPOR to high affinity.

Activation of the EPO receptor results in several biological effects. Three of the activities include stimulation of proliferation, stimulation of differentiation and inhibition of apoptosis (Liboi et al. Proc. Natl. Acad. Sci. USA 90, 11351 (1993); Koury Science 248, 378 (1990)). The signal transduction pathways resulting in stimulation of proliferation and stimulation of differentiation appear to be separable (Noguchi et al. Mol. Cell. Biol. 8, 2604 (1988); Patel et al. J. Biol. Chem. 267, 21300 (1992); Liboi et al. ibid). Some results suggest that an accessory protein may be necessary for mediating the differentiation signal (Chiba et al. Nature 362, 646 (1993); Chiba et al. Proc. Natl. Acad. Sci. USA 90, 11593 (1993)). However there is controversy regarding the role of accessory proteins in differentiation since a constitutively activated form of the receptor can stimulate both proliferation and differentiation (Pharr et al. Proc. Natl. Acad. Sci. USA 90, 938 (1993)).

Activation of the EPO receptor may be due to its dimerization. That is, EPO may act as a crosslinker between two EPO receptor molecules. There is evidence in support of this proposal. An arginine to cysteine mutation at position 129 of the murine EPO receptor results in constitutive activation of the receptor, presumably because of a disulfide bond formed between two receptors subunits (Yoshimura et al. Nature 348, 647 (1990)). In addition EPOR is found in multimeric complexes in cells (Miura & Ihle Arch. Biochem. Biophys. 306, 200 (1993)). However, isolation of a stable multimeric form of purified EPO soluble receptor has not been reported. In addition, dimerization of EPOR may be required, but not by itself be sufficient for complete activation of cells. For example, dimerization may result in a proliferative signal but not a differentiation signal. That is, accessory proteins may be required to send the differentiation signal.

The possible relationship between EPO receptor dimerization and activation may be exploited to identify compounds which are different from EPO but activate the receptor. For example, antibodies possess two identical binding sites for antigen. An anti-EPOR antibody can bind two EPOR molecules and could bring them into close proximity to each other to allow dimerization. In order to function in vivo, these antibodies must recognize the EPOR on surfaces of cells and bind in a way that allows activation of the signal transduction pathway. In addition, it is desirable that activation result in both proliferation and differentiation of erythroid progenitors. A similar approach to understand the activation of human growth hormone receptor (Fuh et al. Science 256, 1677 (1992)) and epidermal growth factor receptor (Schreiber et al. Proc. Natl. Acad. Sci. USA 78, 7535 (1981)) has been reported.

It would be desirable to identify molecules which have the property of activating the EPO receptor and stimulating erythropoiesis. In order to do so, an understanding of the mechanism of EPO receptor activation and signal transduction is important. One approach to elucidating this mechanism may be to identify antibodies which recognize the EPO receptor so as to activate the receptor and stimulate erythropoiesis. Such antibodies are useful in therapeutic and diagnostic applications and would also be useful for probing EPO receptor function.

The following references describe antibodies which bind to the mouse or human EPO receptor:

D'Andrea et al. in *The Biology of Hemtaopoiesis*, Wiley-Liss, Inc. (1990) pp. 153–159, generated polyclonal anti-peptide antibodies against an amino-terminal and a carboxy-terminal peptide of murine EPO receptor. The antibodies were shown to react with mouse EPO receptor in a Western blot.

Bailey et al. Exp. Hematol. 21, 1535–1543 (1993) generated polyclonal anti-peptide antibodies against synthetic peptides homologous to the extraceullular and cytoplasmic domains of the mouse EPO receptor. Receptor activation by these antibodies, as measured by 3H thymidine uptake into spleen cells from phenylhydrazine treated mice, was not detected.

Baynes et al. Blood 82, 2088–2095 (1993) generated a polyclonal antibody to an amino-terminal peptide in the human EPO receptor. The antibody was shown to react with a soluble form of the receptor present in human serum.

D'Andrea et al. Blood 82, 46–52 (1993) generated monoclonal antibodies to human EPO receptor. The antibodies bind to Ba/F3 cells transfected with the human EPO cDNA clone and some inhibit EPO binding and neutralize EPO-dependent growth.

Fisher et al. Blood 82, 197A (1993) used the same monoclonal antibodies as described in D'Andrea, supra to distinguish erythroid progenitor cells having EPO-dependent growth and maturation from those having EPO-independent growth and maturation.

None of the antibodies described in the aforementioned references were reported to activate the EPO receptor or stimulate the growth and/or maturation of erythroid progenitor cells.

Therefore, it is an object of the invention to produce antibodies which recognize an EPO receptor and bind to it such that the receptor is activated. It is a further object of the invention to produce antibodies which bind to an EPO receptor and stimulate erythropoiesis by stimulating the proliferation and/or differentiation of erythroid progenitor cells to erythrocytes. Such antibodies are useful in the treatment of anemia or in the diagnosis of diseases characterized by dysfunctional EPO receptor. Further, such antibodies may lead to the identification of therapeutic agents for the treatment of anemia.

SUMMARY OF THE INVENTION

The invention relates to antibodies or fragments thereof which activate an erythropoietin receptor. Screening of antibodies which recognize the human EPO receptor has revealed that two antibodies, designated Mab 71 and Mab 73, stimulated the proliferation of UT7-EPO cells, an EPO dependent cell line that does not proliferate in the absence of added EPO. Further, Mab 71 stimulated erythroid colony formation from erythroid progenitors in human blood. The antibodies encompassed by the invention may recognize an epitope on an EPO receptor which is recognized by Mab 71 or Mab 73. The antibodies are preferably monoclonal antibodies and may be humanized or human antibodies. Also included are hybridoma cell lines which produce the antibodies of the invention.

Also provided for are methods and kits for detecting EPO receptors in biological samples wherein the methods and kits comprise EPO receptor antibodies of the invention. Pharmaceutical compositions comprising EPO receptor antibodies and pharmaceutically acceptable adjuvants are also encompassed by the invention. Such compositons may be used to treat patients having disorders characterized by low red blood cell levels.

DESCRIPTION OF THE FIGURES

FIG. 7 shows a photograph of purified CD 34$^+$ cells from peripheral blood which were grown 21 days in methylcellulose in the presence of EPO or Mab 71 under serum free growth conditions. Photos are of cells incubated with 500 munits/ml EPO (A), 25 munits/ml EPO (B), or 2.1 micrograms/ml Mab 71 (C).

DETAILED DESCRIPTION OF THE INVENTION

Figure 2:
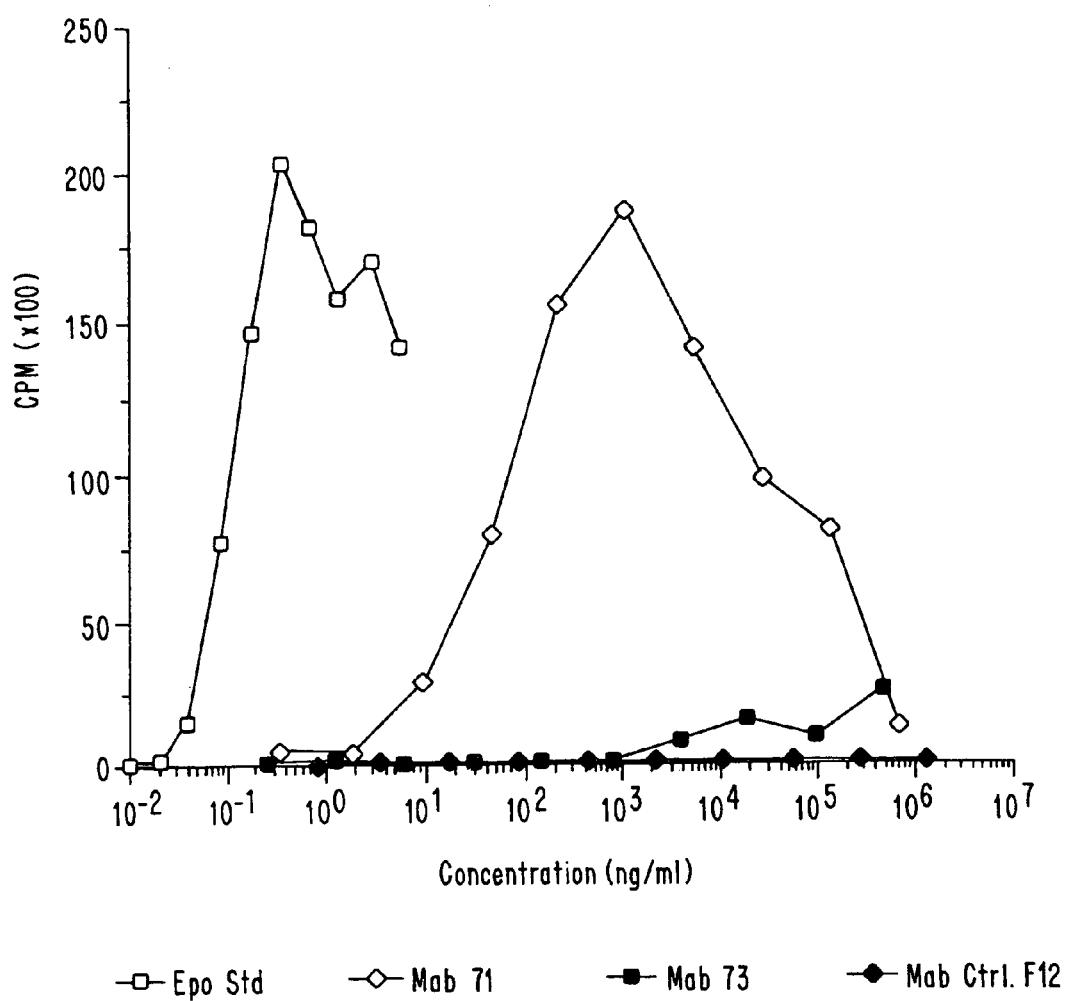
FIG. 2 shows the effect of varying amounts of rHuEPO protein and purified Mabs 71 and 73 on $^3$H thymidine uptake of UT7-EPO cells.

Monoclonal antibodies (Mabs) which recognize the erythropoietin receptor have been generated by immunizing mice with purified soluble human EPO receptor. Soluble human EPO receptor was expressed and purified as described in Examples 1 and 2. Of those Mabs which reacted with soluble human EPO receptor in enzyme-linked immunosorbent assays (ELISAs), 96 mabs were selected for further screening. These mabs were tested for EPO receptor binding by BIAcore analysis (Example 4A) and for binding to EPO receptor on the surface of transfected CHO cells by FACS (Example 4C). The results of these screenings are shown in Table 1. While a number of antibodies bound EPO receptor as determined by BIAcore analysis, only five antibodies of the 96 tested bound EPO receptor displayed on the surface of transfected CHO cells as determined by FACS scanning. 24 antibodies which were positive in ELISA assays (including those five which were positive by FACS scanning) were tested for stimulation of UT7-EPO cell proliferation. Surprisingly, it was found that two antibodies, designated Mab 71 and Mab 73, stimulated the uptake of 3H thymidine into a UT7-EPO cell line (Komatsu et al. Blood 82, 456 (1993)) in the absence of EPO (Example 8A). The UT7-EPO cell line requires the presence of EPO in its medium for growth. Therefore, the stimulation of UT7-EPO cell growth is likely due to the activation of EPO receptor by Mab 71 and Mab 73. As shown in FIG. 2, the response of UT7-EPO cells was greater in the presence of Mab 71 than Mab 73. It was further found that Mab 71 stimulated erythroid colony formation from human erythroid precursors (see Example 9). This is the first instance of an antibody stimulating the formation of erythroid colonies from erythroid precursors.

Figure 5:
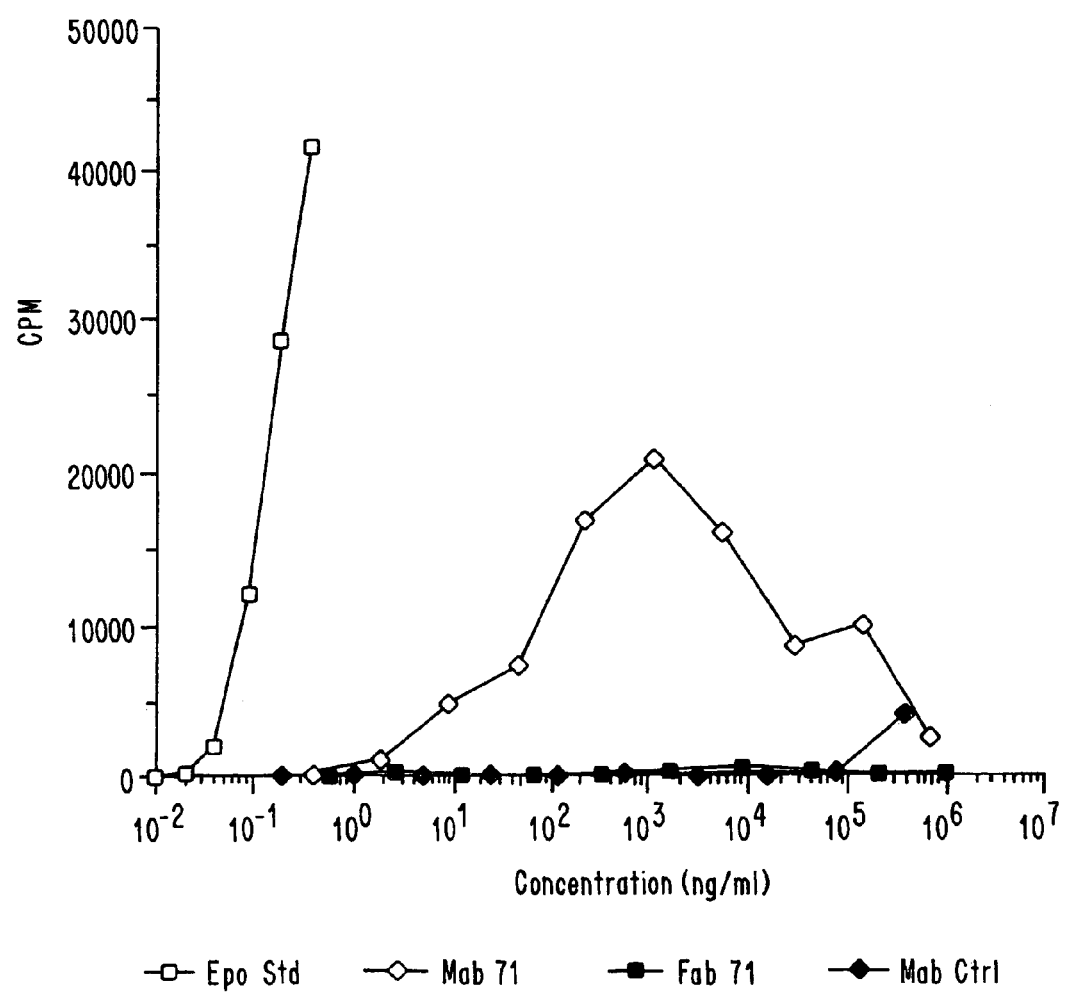
FIG. 5 shows the effect of varying amounts of purified rHuEPO protein, Mab 71 or Fab 71 on $^3$H thymidine uptake of UT7-EPO cells.

The invention provides for an antibody or fragment thereof which activates an erythropoietin receptor. As used herein, the term "activation of an EPO receptor" denotes one or more molecular processes which an EPO receptor undergoes that result in transduction of a signal to the interior of a receptor-bearing cell, wherein the signal ultimately brings about one or more changes in cellular physiology. Cellular responses to EPO receptor activation are typically changes in the proliferation or differentiation of receptor-bearing cells. Receptor-bearing cells are typically erythroid progenitor cells. Presently, the molecular events leading to signal transduction by EPO receptor are poorly understood. However, as indicated in the background, some evidence suggests that EPO receptor dimerization is at least one event which is likely to be required for activation. The present disclosure also provides support for this idea. As shown in FIG. 5, stimulation of 3H-thymidine uptake in UT7-EPO cells by Mab 71 is abolished when substituted by the corresponding Fab fragment designated Fab 71. Therefore, replacement of the intact, bivalent antibody with a corresponding monovalent fragment eliminates the proliferative response. In addition Mab 71 inhibits activation of the EPO receptor at high concentrations. Both of these observations support the dimerization model of activation for the EPO receptor. Mab 71 has been shown to interact with a synthetic peptide of residues 49 to 78 of the human EPO-R (see example 6). Thus this region of EPO-R when bound by a cross linker such as Mab 71 can result in activation of EPO-R. It is understood that molecules that cross-link two EPO-R molecules by binding to residues 49 to 78 are also encompassed by the invention. These molecules could be antibodies or other bivalent molecular entities that have the property of crosslinking two EPO receptors by binding to residues contained within the region between residues 49 and 78 thereby resulting in dimerization and activation of the EPO receptor.

EPO receptors of the invention will preferably be mammalian EPO receptors and, in a particularly preferred embodiment, will be human EPO receptor. It is understood that analogs of human EPO receptors are also encompassed by the invention. Such analogs are constructed by insertions, deletions, extensions or substitutions of amino acids in the human EPO receptor sequence. Examples of EPO-R analogs have been described in U.S. Pat. No. 5,292,654 to Yoshimura et al. wherein substitution of a cysteine residue at position 129 of the EPOR amino acid sequence resulted in constitutively activated EPOR. In general, EPO-R analogs having amino acids changes in regions other than the antibody binding domains necessary for activation wherein said analogs retain secondary and tertiary structure of the human EPO receptor may be recognized by the antibodies of the present invention. It has been shown that Mab 71 interacts with a synthetic peptide of residues 49 to 78 of the human EPO-R (see Example 6). Therefore, EPO-R analogs having changes in amino acid residues other than those at positions 49 to 78 and retaining the human EPO receptor secondary and tertiary structure are likely to be recognized by Mab 71. The numbering of amino acid residues in the human EPOR polypeptide as used herein starts with proline at position 1, which is the amino terminal residue after cleavage of the 25 amino acid signal peptide.

Antibodies of the invention bind to an epitope on an EPO receptor which is involved in receptor activation. In one embodiment, antibodies recognize an epitope on an EPO receptor which is recognized by Mab 71 or an epitope which is recognized by Mab 73. Mab 71 recognizes a synthetic peptide spanning amino acid residues 49 to 78 in the human EPO-R. Therefore, it is likely that Mab 71 recognizes an epitope on EPO-R which is defined in whole or in part by this sequence. As used herein, the term "epitope" refers to the region of an EPO-R bound by an antibody wherein the binding prevents association of a second antibody to an EPO-R.

The invention also provides polyclonal antibodies, and monoclonal antibodies and fragments thereof. Antibody fragments encompass those fragments which activate an EPO receptor. Also encompassed are humanized antibodies, typically produced by recombinant methods, wherein human sequences comprise part or all of an antibody which activates an EPO receptor. Examples of humanized antibodies include chimeric or CDR-grafted antibodies (U.S. Pat. Nos. 4,816,567 and 5,225,539). Also included are fully human antibodies to EPO receptor produced in genetically-altered mice (see PCT Application No. 93/12227). Antibodies of the invention may also have a detectable label attached thereto. Such a label may be a fluorescent (e.g., fluorescein isothiocyanate, FITC), enzymatic (e.g, horseradish peroxidase), affinity (e.g., biotin) or isotopic label (e.g., $^{125}$I).

Also encompassed by the invention are hybridoma cell lines producing a monoclonal antibody which activates an EPO receptor. In one embodiment, the hybridoma cell line produces a monoclonal antibody which recognizes an epitope on an EPO receptor which is recognized by Mab 71 or Mab 73. Generation of hybridoma cell lines producing monoclonal antibodies to human EPO-R are described in example 3. The hybridoma cell line which produces Mab 71 has been deposited with the American Type Culture Collection, 10801 University Boulevard, Manassas, VA 20110-2209 on Jul. 26, 1994 under accession no. HB 11689. The hybridoma cell line which produces Mab 73 has been deposited with the American Type Culture Collection, 10801 University Boulevard. Manassas, VA 20110-2209 on Jul. 26, 1994 under accession no. HB 11690.

The antibodies of the present invention are useful in diagnosing anemia and other diseases characterized by dysfunctional EPO-R. In one embodiment, a method of detecting in a biological sample an EPO receptor which is capable of being activated comprising the steps of: (a) contacting the sample with an antibody which activates an EPO receptor; and (b) detecting activation of the receptor by the antibody. The biological samples include tissue specimens, intact cells, or extracts thereof. Antibodies may be used as part of a diagnostic kit to detect the presence of EPO receptors in a biological sample. Such kits employ antibodies having an attached label to allow for detection. The antibodies are useful for identifying normal or abnormal receptors. the presence of abnormal receptors in a biological sample may be indicative of disorders such as Diamond Blackfan anemia, where it is believed that the EPO receptor is dysfunctional.

The antibodies of the present invention are useful in diagnosing anemia and other diseases characterized by dysfunctional EPO-R. In one embodiment, a method of detecting in a biological sample an EPO receptor which is capable of which being activated comprising the steps of: (a) contacting the sample with an antibody which activates an EPO receptor; and (b) detecting activation of the receptor by the antibody. The biological samples include tissue specimens, intact cells, or extracts thereof. Antibodies may be used as part of a diagnostic kit to detect the presence of EPO receptors in a biological sample. Such kits employ antibodies having an attached label to allow for detection. The Antibodies of the invention are useful for treating disorders characterized by low red blood cell levels. Included in the invention are methods of modulating the endogenous activity of an EPO receptor in a mammal, preferably methods of increasing the activity of an EPO receptor. In general, any condition treatable by erythropoietin, such as anemia, may also be treated by the antibodies of the invention. Therapeutic antibodies are administered by an amount and route of delivery that is appropriate for the nature and severity of the condition being treated and may be ascertained by one skilled in the art. Preferably, administration is by injection, either subcutaneous, intramuscular, or intravenous.

The invention provides for a pharmaceutical composition comprising a therapeutically effective amount of an antibody which activates an EPO-R together with a pharmaceutically acceptable adjuvant, wherein the adjuvant may be selected from one or more of a diluent, carrier, preservative, emulsifier, anti-oxidant and/or stabilizer. A "therapeutically effective amount" as used herein refers to that amount of antibody which provides a therapeutic effect for a given condition and administration regimen. In the present invention, the therapeutic effect is stimulation of red blood cell production as evidenced by a rise in hematocrit in the patient being treated. In a preferred embodiment, the antibodies are humanized or human antibodies which may be prepared using procedures known to the skilled worker. Pharmaceutically acceptable adjuvants are known to one skilled in the art and are surveyed extensively in Remington's Pharmaceutical Sciences, 18th ed. A. R. Gennaro, ed. Mack, Easton, Pa. (1990).

The following examples are offered to more fully illustrate the invention, but are not construed as limiting the scope thereof.

EXAMPLE 1

Production of Soluble Human Erythropoietin Receptor

A. Isolation of Clones for Expression of Soluble Human Erythropoietin Receptor.

Using a clone containing the human erythropoietin receptor as described by Jones et al. supra, the PCR technique was used to obtain a clone for expression of soluble human erythropoietin receptor (sHuEPOR). Primers for PCR amplification of human erthropoietin receptor were:

```
5' primer:                                                  (SEQ. ID NO:1)
5'-CTC CAA GCT TGC CGT CAC CAT GGA CCA CCT CGG GGC GTC CCT-3';
and 3' primer:                                                  (SEQ. ID NO:2)
5'-CAG GTC TAG ATT ACT AGG GAT CCA GGT CGC TAG GC-3'
```

PCR reactions were carried out using 2.5 ng of a plasmid containing human EPOR, 5 pmol of each of the above oligonucleotide primers, 10 mM Tris HCl (pH 8.3), 50 mM KCl, 1.5 mM Mg Cl$_2$, 200 µM each dNTP and 1 unit of Taq polymerase. Amplification was for 5 cycles of 30 sec. at 94° C., 1 min. at 50° C., 1 min at 72° C., followed by 20 cycles of 30 sec. at 94° C., 1 min. at 55° C., 1 min at 72° C. DNA was purified by passage through a G-50 size exclusion column (Boehringer Mannheim Corp.), then digested with Hind III and XbaI and ligated into the expression vector pDSRα2 (DeClerck et al. J. Biol. Chem. 266, 3893 (1991)) which has also been digested with Hind III and XbaI. Clones containing the desired insert were verified by DNA sequence analysis.

The d40EPOR clone was made by PCR from a full length human EPOR clone (see above). The carboxy terminus of d40EPOR is tyr467, the result of adding a stop codon within the primer. Primers for PCR amplification were:

5' primer: (SEQ. ID NO:1)
5'-CTC CAA GCT TGC CGT CAC CAT GGA CCA CCT CGG GGC GTC CCT-3';
and 3' primer: (SEQ. ID NO:3)
5'-AGG TCG ACT ACT AGT AGT CAG TTG AGA-3'

PCR amplification used pfu polymerase in pfu buffer2 (Stratagene, La Jolla, CA). Reaction conditions were: 1 cycle at 96° for 30 sec., 45° for 1 mim., 72° for 1 min.; 25 cycles at 96° for 1 mim., 55° for 1 mim., 72° for 2 mim. A final 72° incubation for 5 mim. was then performed. The reaction products were separated by agarose gel electrophoresis and the approximately 1.3 Kb band was isolated using a GENECLEAN® kit ( BIO 101, Vista, CA.). The purified fragment was ligated into PCR II (TA cloning kit, Invitrogen, San Diego, CA). Recombinants were identified by restriction analysis and sequenced to confirm the desired inserts were present. A HindIII-SalI fragment was isolated as described above and ligated into an isolated pDSRα2 vector that had been previously cut with HindIII and SalI. The resultant vector, pDSRαEPORd40 was used for expression in CHO cells.

B. Expression of Soluble Human EPOR and d40 EPOR in CHO Cells

The expression plasmid pDSRα2-EPOR-X contains sequences encoding human EPOR amino acids Met1-Pro249 as shown in Jones et al. supra. Plasmid pDSRαEPORd40 contains sequences encoding Met1-Tyr467. Ten micrograms of each plasmid were independently introduced into CHO cells by calcium phosphate mediated transfection (Wigler et al. Cell 11, 233 (1977)). Individual colonies were selected based upon expression of the dihydrofolate reductase gene from the vector. Expression of human EPOR was monitored by RNA hybridization (Hunt et al., Exp. Hematol, 19: 779 (1991)) and by Western immuno blotting using an affinity purified antibody. Cell lines which were positive in these assays were selected for further expansion. Cell lines were adapted to 30 nM Methotrexate (Mtx) to stimulate amplification of EPO-R expression.

Generation of conditioned media containing soluble human EPOR was done in both roller bottles and a hollow fiber bioreactor. Roller bottles were innoculated with 2×10⁷ cells in 200 ml growth medium (DMEM: Ham's F12 (1:1) supplemented with non-essential amino acids (NEAA), 30 nM Mtx and 5% fetal bovine serum (FBS) (reagents from GIBCO, Grand Island, N.Y.)). Upon reaching confluence in 3–4 days, the media was replaced with 200 ml DMEM: Ham's F12, NEAA, 30 nM Mtx with no serum. Conditioned media was harvested after 6–7 days and replaced with fresh serum-free media. Second and third harvests were collected.

A Cell Pharm bioretor cartridge was innoculated with 5×10⁸ cells in growth medium (as above) supplemented with 5 μg/mL gentamicin. The pH was maintained at 7.3. Beginning on day 12 after innoculation the cells were weaned off of serum to generate serum-free conditioned media. Harvesting of conditioned media began on day 17.

EXAMPLE 2

Purification of Soluble Human Erythropoietin Receptor

Four different preparations of soluble recombinant human EPOR were made. In the first preparation, Epoxy-activated Sepharose 6B (Pharmacia, Piscataway, N.J.) is coupled with recombinant human erythropoietin (rHuEPO) essentially as per manufacturer's instructions. 218 mg of rHuEPO in 4.5 mL of 32 m$\underline{M}$ ZnCl$_2$ is added to 7.2 g of Epoxy-activated Sepharose 6 B previously hydrated and washed with H2O. This slurry is titrated to pH 10.8 then mixed overnight at room tempurature. Any remaining reactive groups are then blocked by addition of ethanolamine to a final concentration of 1 $\underline{M}$ and mixed for 4 hours at room temperature. The subsequent steps are performed at 8°±20° C. The coupled resin (Epoxy-EPO) is packed into a column and washed with alternating cycles of 0.5 $\underline{M}$ NaCl/0.1 $\underline{M}$ HOAc pH 4 and 0.5 $\underline{M}$ NaCl/0.1 $\underline{M}$ Borate pH 8. The column is equilibrated with 140 m$\underline{M}$ NaCl/10 m$\underline{M}$ Tris pH 7.6 (TBS). It is loaded with 1560 mL of roller bottle produced conditioned media from CHO cells expressing soluble EPO-R (sHuEPO-R). After loading is complete, the column is washed with 300 m$\underline{M}$ NaCl/10 m$\underline{M}$ Tris pH 7.6 then the bound sHuEPOR is eluted with 1 $\underline{M}$ NaCl/3 $\underline{M}$ urea/10 m$\underline{M}$ Tris pH 7.6. Two UV$_{280}$ absorbing peaks elute with this buffer. The second peak to elute, which contains the sHuEPOR, is pooled and diluted 20 fold with H$_2$O. The diluted pool is then loaded to a 1 mL prepacked column of Mono Q (Pharmacia) and eluted with a NaCl gradient in 10 m$\underline{M}$ Tris pH 7.6. A single peak elutes, which is pooled, aliquoted and stored frozen at −80° C.

In the second preparation, a larger Epoxy-EPO column is made. 20.4 g of Epoxy-activated Sepharose 6 B is hydrated and washed with H$_2$O, then with acetone and finally with 50% formamide in H$_2$O pH 10.6. 729 mg of rHuEPO in 15 mL of H$_2$O is titrated to pH 10.6, added to the resin and mixed overnight at room tempurature. Any remaining reactive groups are then blocked by addition of ethanolamine to a final concentration of 1 $\underline{M}$ and mixed for 140 minutes at room temperature. The subsequent steps are performed at 8°±2° C. The Epoxy-EPO is packed into a column and washed with 3 $\underline{M}$ urea/750 m$\underline{M}$ NaCl/10 m$\underline{M}$ Tris pH 7.6, the column is then equilibrated with TBS. 100 mL of bioreactor produced conditioned media from CHO cells expressing sHuEPOR are mixed with 2 mL of Q Sepharose Fast Flow (Pharmacia). It is incubated for 30 minutes at 8°±2° C. with frequent mixing, then filtered through a 0.45 micron cellulose nitrate bottle top filter (Corning). The filtrate is loaded to the Epoxy-EPO column, washed with 250 m$\underline{M}$ NaCl/10 m$\underline{M}$ Tris pH 7.6, then eluted with 3 $\underline{M}$ urea/750 m$\underline{M}$ NaCl/10 m$\underline{M}$ Tris pH 7.6. The eluted peak is pooled and diluted 20 fold with H$_2$O. The diluted pool is then loaded to a 15 mL column of Q Sepharose Fast Flow and eluted with a NaCl gradient in 10 m$\underline{M}$ Tris pH 7.6. The single peak that elutes is pooled, aliquoted and stored frozen at −80° C.

In the third preparation, the same Epoxy-EPO column used in preparation 2 is used. 850 mL of roller bottle produced conditioned media from CHO cells expressing sEPO-R are mixed with 1.7 mL of Q Sepharose Fast Flow. It is processed in the same manner as is done in preparation 2.

In the fourth preparation, 7.25 L of bioreactor produced conditioned media from CHO cells expressing sHuEPOR are mixed with 110 mL of Q Sepharose Fast Flow. It is incubated for 1 hour at 8°±2° C. with frequent mixing, then filtered through a 0.45 micron cellulose nitrate bottle top filter The filtrate is then diluted with 7.25 L of $H_2O$ and loaded to a 770 mL column of Q Sepharose Fast Flow equilibrated in 20 m$\underline{M}$ Tris pH 7.6. The column is eluted with a NaCl gradient in 20 m$\underline{M}$ Tris pH 7.6. Fractions containing significant amounts of sHuEPOR based on SDS-PAGE analysis are pooled. Solid $(NH_4)_2SO_4$ is added to the pool to a final concentration of 1.2 $\underline{M}$ then filtered through a 0.45 micron cellulose nitrate bottle top filter The filtrate is loaded to a 60 mL column of Phenyl Sepharose 6 (low sub, Pharmacia) and eluted with a decreasing gradient of 1.2 $\underline{M}$to 0 $\underline{M}$ $(NH_4)_2SO_4$ in 20 m$\underline{M}$ Tris pH 7.6. The major eluting peak is pooled and made 2.4 $\underline{M}$ in $(NH_4)_2SO_4$ to precipitate the sHuEPORt. The precipitated sHuEPOR is harvested by centrifugation, resuspended with $H_2O$ and titrated to pH 7.9 with Tris-HCl. The resultant solution is filtered through a 0.45 micron cellulose nitrate filter, aliquoted and stored frozen at −80° C.

EXAMPLE 3

Preparation and Screening of Hybridoma Cell Lines

A. Enzyme-linked Immunosorbent Assay (EIA)

EIAs were initially performed to determine serum antibody (Ab) titres of individual animals, and later for screening of potential hybridomas. Flat bottom, high-binding, 96-well microtitration EIA/RIA plates (Costar Corporation, Cambridge, Mass.) were coated with purified sHuEPOR at 5 μg per ml carbonate-bicarbonate buffer, pH 9.2 (0.015 M $Na_2CO_3$, 0.035 M $NaHCO_3$). Fifty μl of the Ab were added to each well. Plates were then covered with acetate film (ICN Biomedicals, Inc., Costa Mesa. Calif.) and were incubated at room temperature (RT) on a rocking platform for 2 hours or over-night at 4° C. sHuEPOR lot #1 was used after the first and second boost, lot #2 was used after the third boost. sHuEPOR lots #3 and 4 were used for screening of hybridomas. Plates were blocked for 30 minutes at RT with 250 μl per well 5% BSA solution prepared by mixing 1 part BSA diluent/blocking solution concentrate (Kirkegaard and Perry Laboratories, Inc.) with 1 part deionized water ($dH_2O$). Blocking solution having been discarded, 50 μl of serum 2-fold dilutions (1:400 through 1:51,200) or hybridoma tissue culture supernatants were added to each well. Serum diluent was 1% BSA (10% BSA diluent/blocking solution concentrate diluted 1:10 in Dulbecco's Phosphate Buffered Saline, D-PBS; Gibco BRL, Grand Island, N.Y.), while hybridoma supernatants were tested undiluted. In the case of hybridoma testing, one well was maintained as a conjugate control, and a second well as a positive Ab control. Plates were again incubated at RT, rocking, for 1 hour, then washed 4 times using a 1× preparation of wash solution 20× concentrate (Kirkegaard and Perry Laboratories, Inc.) in $dH_2O$. Goat anti-mouse IgG heavy- and light-chain specific horseradish peroxidase conjugated secondary Ab (Boehringer Mannheim Biochemicals, Indianapolis, Ind.) diluted 1:1000 in 1% BSA was then incubated in each well for 30 minutes. Plates were washed as before, blotted dry and ABTS Peroxidase single component substrate (Kirkegaard and Perry Laboratories, Inc.) was added. Absorbance was read at 405 nm for each well using a Microplate EL310 reader (Bio-tek Instruments, Inc., Winooski, Vt.). Half-maximal titre of serum antibody was calculated by plotting the $log_{10}$ of the serum dilution versus the optical density at 405 nm, then extrapolating at the 50% point of the maximal optical density obtained by that serum. Hybridomas were selected as positive if optical density scored greater than 5-fold above background.

B. Immunization

Ten, 4.5-week old Balb/c mice (Charles Rivers Laboratories, Wilmington, Mass.) were subcutaneously injected (SQI) with 50 μg sHuEPOR; lot 1; antigen) emulsified in Complete Freund's Adjuvant (CFA; 50% vol/vol; Difco Laboratories, Detroit, Mich.). These animals were boosted (SQI) 4 weeks later with 25 μg antigen (Ag; lot 1) prepared in similar fashion using Incomplete Freund's Adjuvant (ICFA; Difco Laboratories, Detroit, Mich.). Mice were bled via the tail 9 days later and serum antibody (Ab) titres determined by enzyme-linked immunosorbent assay (EIA). As the ½ maximal titre for each mouse rose above 5000, individual animals were selected for the hybridoma preparation. The three animals (#7, 8 and 9) which were used to generate the hybrids of interest (#71A and 73A) required additional boosts at 5 weeks and again at 29 weeks using 12.5 μg Ag (lot 1) and 25 μg Ag (lot 2) respectively. These boosts were performed in the same manner as the initial boost; that is, as an emulsion in 50% vol/vol ICFA. Serum Ab titres continued to be monitored 9 days following each boost. The final titres of these mice prior to fusion were 5026, 6842, and 12,945 for animals 7, 8 and 9, respectively.

C. Cell Fusion

Animals 7, 8 and 9 were intravenously injected with 25 μg of sHuEPOR (lot #3) 8 weeks following the final boost. Four days later, mice were sacrificed by carbon dioxide and spleens collected under sterile conditions into 25 ml Dulbecco's Modified Eagle's Medium containing 200 U/ml Penicillin G, 200 μ/ml Streptomycin sulfate, and 4 mM glutamine (2× P/S/G DMEM). The spleens were trimmed of excess fatty tissue, then rinsed through 3 dishes of clean 2× P/S/G DMEM. They were next transferred to a sterile stomacher bag (Tekmar, Cincinnati, Ohio) containing 10 ml of 2× P/S/G DMEM, and disrupted to single cell suspension with the Stomacher Lab Blender 80 (Seward Laboratory UAC House; London, England). As cells were released from the spleen capsule into the media, they were removed from the bag and passed through a 70 μm nylon mesh cell strainer (Becton Dickinson and Company; Lincoln Park, N.J.). Fresh media was replaced in the bag and the process continued until the entire cell content of the spleens were released. These splenocytes were washed 3 times by centrifugation at 225× g for 10 minutes. In the first fusion, splenocytes from animal #9 were used; in the second fusion, splenocytes from animals #7 and 8 were pooled.

Concurrently, log phase cultures of Sp2/0-Ag14 mouse myeloma cells (available from the American Type Culture Collection, Rockville, Md. under accession no. CRL 1581) grown in complete medium (DMEM, 10% fetal bovine serum, 2 mM glutamine, 0.1 mM non-essential amino acids, 1 mM sodium pyruvate, and 10 mM Hepes Buffer; Gibco Laboratories, Inc., Grand Island, N.Y.), were washed in similar fashion. From this myeloma population, $4×10^7$ cells (fusion 1) or $8×10^7$ cells (fusion 2) were taken, mixed with the suspension of splenocytes, and pelleted once again. The media was aspirated from the cell pellet and 2 ml of polyethylene glycol (PEG 1500 MWt; Boehringer Mannheim Biochemicals, Indianapolis, Ind.) for fusion 1 of 3.5 ml of PEG for fusion 2 at 37° C. were gently mixed into the media over the course of 1 minute. Thereafter, an equal volume of 2× P/S/G DMEM was slowly added. The cells were allowed to rest at 37° C. for 2 minutes, then an additional 9 ml of 2× P/S/G DMEM added. The cells were again set at 37° C. for 4 minutes. Finally, 30 ml of 2× P/S/G DMEM was added to the cell suspension, and the cells pelleted by centrifugation. Media was aspirated from the pellet and the cells gently resuspended into approximately 56 ml (fusion 1) or 74 ml (fusion 2) of complete medium containing 100 U/ml Penicillin G and 100 µ/ml Streptomycin Sulfate. Cells were distributed over 10 96-well flat bottom tissue culture plates (Becton Dickinson Labware; Lincoln Park, N.J.) by single drops from a 5 ml pipette. Plates were incubated in humidified conditions at 37° C., 5% $CO_2$, overnight. The next day, an equal volume of selection medium was added to each well. Selection consisted of 0.1 mM hypoxanthine, $4\times10^{-4}$ mM aminopterin, and $1.6\times10^{-2}$ mM thymidine in complete medium. The fusion plates were incubated for 7 to 10 days with 2 changes of medium during this time; HAT selection medium was used after each fluid change. Tissue culture supernatants were taken from each hybrid-containing well and tested by EIA for specific antibody reactivity to sHuEPOR. 96 wells which were positive in EIA were subjected to further screening.

D. Dot Blots

Dot blots of reduced sHuEPOR (lot #4) were used as a secondary screening method for EIA positive hybridomas. The Dot Blot SF Microtitration Apparatus (Bio-Rad Laboratories, Inc.; Richmond, Calif.) was set-up according to the instruction manual; nitrocellulose membranes (9×12 cm; Bio-Rad Laboratories, Inc.; Richmond, Calif.) were employed. Antigen was first prepared by boiling for 5 minutes under reducing conditions with 2-mercaptoethanol (5% vol/vol; Bio-Rad Laboratories, Inc.; Richmond, Calif.) in Tris-buffered saline solution (TBS; 10 mM Tris pH 7.5, 154 mM NaCl, 0.01% wt/vol Na azide). Twenty-five ng of sHuEPOR (lot #4) was loaded into each well and aspirated through the nitrocellulose membrane for binding. The wells were filled with 250 µl Blotto-Tween solution (block solution; 2% wt/vol non-fat dry milk, 50 mM Tris, pH 7.5, 25 mM NaCl, 0.1 mM EDTA, 0.09% vol/vol Tween 20, 0.01% vol/vol anti-foam A) and incubated at RT for 30 minutes. Block solution was aspirated from the wells and the procedure repeated for a second time to ensure complete blocking of non-specific sites on the membrane. This was followed by 3 washes through the membrane with D-PBS containing 0.1% vol/vol polyoxyethylene sorbitan monolaurate (Tween-20; Bio-Rad Laboratories, Inc.; Richmond, Calif.). Ninety-five µl of EIA-positive hybridoma conditioned medium was next added to each well and incubated for 45 minutes at RT. Wells were washed 3× with TBS-Tween (20 mM Tris, pH 7.5, 50 mM NaCl, 0.02% vol/vol Tween 20) and 2× with TBS-Tween (20 mM Tris, pH 7.5 0.5 M NaCl, 0.09% vol/vol Tween 20) at 250 µl per wash, aspirating through the membrane after each addition. One-hundred µl of goat anti-mouse IgG, heavy- and light-chain specific, HRP-conjugated secondary antibody (1:1000 diluted in TBS-Tween; Boehringer Mannheim Biochemicals; Indianapolis, Ind.) was incubated in each well for 45 min at RT. Membranes were washed as before, removed from the blot apparatus, dipped into prepared Enhanced Chemiluminescent Reagent (ECL reagent; Amersham Life Sciences, Corporation; Arlington Heights, Ill.), and exposed to X-OMAT AR film (Kodak Scientific Imaging, Rochester, N.Y.). Fifteen seconds later, the film was removed from film cassettes and developed. Each well was scored 3+ to 0 based on intensity of dots for individual hybridoma supernatants.

EXAMPLE 4

Anti-EPOR Antibody Binding to EPOR

A. Antibody Binding to EPO-R by BIAcore Analysis

Real-time biospecific interaction analysis (BIA, Pharmacia Biosensor AB, Uppsala, Sweden) based on surface plasmon resonance (SPR) (Fiagerstam et al. J. Mol. Recognition 3, 208 (1990); Malmbory et al. Scand. J. Immunol. 35, 643 (1992)) was used to screen the ELISA positive monoclonal antibodies.

Soluble HuEPOR prepared as described in Examples 1 and 2 was covalently coupled to the sensor chip CM5 via the primary amine group. The immobilization was performed at a flow of 5 ul/min in HBS (10 mM HEPES pH 7.4, 150 mM NaCl, 3.4 mM EDTA, 0.05% BIAcore surfactant P-20). The carboxylated matrix of the sensor chip was first activated with a 40 ul injection of 1:1 mixture of EDC (400 mM N-ethyl-N-(dimethylamine-propyl)carbodiimide in water, Pharmacia Biosensor AB) and NHS (100 mM N-hydroxysuccinimide in water, Pharmacia Biosensor AB). 65 ul of soluble EPO-R(50 ug/ml in 10 mM Na-acetate pH4.0) was injected to immobilize onto the sensor chip. The excess reactive groups of the sensor chip were deactivated with an injection of 50 ul of ethanolamine (Pharmacia Biosensor AB). Each analysis cycle included an injection of 20 ul of hybridoma supernatant,followed by injection of 10 ul of 10 mM HCl for regeneration of the chip. The SPR response is measured in Resonance Units (RU). For most proteins,1000 RU corresponds to a surface concentration of approximately 1 ng/mm². Results of screening 96 wells which were positive in EIAs are shown in Table 1. In these experiments, background is typically about 20 RU. Binding to EPOR is significant at 50 RU and above.

TABLE 1

EPO-R Monoclonal Antibodies

| ANTIBODY (1) | BIACORE (2) | BIACORE (3) COMPETITION GROUP | FACS (4) MEAN FLOURESCENCE | Inhibition of EPO Activity (5) | Stimulation of UT7-EPO Cells (6) |
|---|---|---|---|---|---|
| 1 | 98 | A | — | - | - |
| 2 | 8 | NT | — | NT | NT |
| 3 | 7 | NT | — | NT | NT |
| 4 | 65 | NT | — | NT | NT |
| 5 | 13 | NT | — | NT | NT |
| 6 | 9 | NT | — | - | - |
| 7 | 89 | C | — | NT | NT |
| 8 | 46 | NT | — | NT | NT |
| 9 | 29 | NT | — | NT | NT |
| 10 | 69 | NT | — | NT | NT |

TABLE 1-continued

EPO-R Monoclonal Antibodies

| ANTIBODY (1) | BIACORE (2) | BIACORE (3) COMPETITION GROUP | FACS (4) MEAN FLOURESCENCE | Inhibition of EPO Activity (5) | Stimulation of UT7-EPO Cells (6) |
|---|---|---|---|---|---|
| 11 | 4 | NT | — | NT | NT |
| 12 | 153 | C | — | NT | NT |
| 13 | 1499 | B | — | NT | NT |
| 14 | 87 | NT | — | NT | NT |
| 15 | 29 | NT | — | NT | NT |
| 16 | 8 | NT | — | NT | NT |
| 17 | 7 | NT | — | NT | NT |
| 18 | 46 | NT | — | - | - |
| 19 | 9 | NT | — | NT | NT |
| 20 | 7 | NT | — | NT | NT |
| 21 | 49 | NT | — | NT | NT |
| 22 | 8 | NT | — | NT | NT |
| 23 | 4 | NT | — | - | - |
| 24 | 26 | NT | — | NT | NT |
| 25 | 8 | NT | — | NT | NT |
| 26 | 84 | NT | — | NT | NT |
| 27 | 2 | NT | — | NT | NT |
| 28 | 11 | NT | — | NT | NT |
| 29 | 1 | NT | — | NT | NT |
| 30 | 270 | A | — | - | - |
| 31 | 16 | NT | — | - | NT |
| 32 | 18 | NT | — | NT | NT |
| 33 | 15 | NT | — | NT | NT |
| 34 | 25 | NT | — | NT | NT |
| 35 | 363 | A | — | NT | NT |
| 36 | 4 | NT | — | NT | NT |
| 37 | 16 | NT | — | - | - |
| 38 | 13 | NT | — | NT | NT |
| 39 | 574 | B | — | - | - |
| 40 | 15 | NT | — | NT | NT |
| 41 | 22 | NT | — | NT | NT |
| 42 | 23 | NT | — | NT | NT |
| 43 | 6 | NT | — | NT | NT |
| 44 | 13 | NT | — | NT | NT |
| 45 | 13 | NT | — | NT | NT |
| 46 | 7 | NT | — | NT | NT |
| 47 | 10 | NT | — | NT | NT |
| 48 | 5 | NT | — | NT | NT |
| 49 | 69 | NT | — | NT | NT |
| 50 | 345 | C | — | - | - |
| 51 | 31 | NT | — | NT | NT |
| 52 | 6 | NT | — | NT | NT |
| 53 | 130 | A | — | NT | NT |
| 54 | 13 | NT | — | NT | NT |
| 55 | 34 | NT | — | NT | NT |
| 56 | 11 | NT | — | NT | NT |
| 57 | 10 | NT | — | NT | NT |
| 58 | 15 | NT | 14.99 | + | ? |
| 59 | 10 | NT | — | NT | NT |
| 60 | 10 | NT | — | NT | NT |
| 61 | 48 | NT | — | NT | NT |
| 62 | 814 | A | — | - | - |
| 63 | 1539 | B | — | NT | NT |
| 64 | 1222 | C | — | NT | NT |
| 65 | −5 | NT | — | +/− | ? |
| 66 | 975 | C | — | NT | NT |
| 67 | 1000 | A | — | - | ? |
| 68 | 495 | C | — | NT | NT |
| 69 | 877 | A | — | - | - |
| 70 | 789 | A | — | - | ? |
| 71 | 1584 | C | 23.55 | + (7) | +++ |
| 72 | 1190 | B | — | - | - |
| 73 | 354 | C | 13.71 | - | + |
| 74 | 408 | A | 18.53 | - | - |
| 75 | 947 | B | — | NT | NT |
| 76 | 6 | NT | — | NT | NT |
| 77 | 434 | C | — | - | - |
| 78 | 119 | A | — | NT | NT |
| 79 | 8 | NT | — | NT | NT |
| 80 | 11 | NT | — | NT | NT |
| 81 | −4 | NT | — | NT | NT |
| 82 | 4 | NT | — | NT | NT |
| 82B | −13 | NT | NT | NT | NT |

TABLE 1-continued

EPO-R Monoclonal Antibodies

| ANTIBODY (1) | BIACORE (2) | BIACORE (3) COMPETITION GROUP | FACS (4) MEAN FLOURESCENCE | Inhibition of EPO Activity (5) | Stimulation of UT7-EPO Cells (6) |
|---|---|---|---|---|---|
| 83 | 1025 | C | — | - | - |
| 84 | 5 | NT | — | NT | NT |
| 85 | 11 | NT | — | NT | NT |
| 86 | 859 | C | — | NT | NT |
| 87 | 4 | NT | 12.81 | - | - |
| 88 | 4 | NT | — | +/- | - |
| 89 | -1 | NT | — | +/- | - |
| 90 | 4 | NT | — | NT | NT |
| 91 | 0 | NT | — | - | - |
| 92 | -3 | NT | — | NT | NT |
| 93 | 2 | NT | — | NT | NT |
| 94 | 5 | NT | — | NT | NT |
| 95 | 417 | A | — | NT | NT |
| 96 | 7 | NT | — | NT | NT |

Tissue culture medium conditioned by hybridomas secreting the indicated antibodies were tested with the assays indicated. Supernatants containing all the antibodies shown gave a positive signal in ELISA assays.
+++, ++, + indicate a positive response with +++ indicating those having the greatest effect.
– indicates a response less than or equal to the response of control medium.
NT indicates samples were not tested.
? indicates samples that could not be assigned a response.
(1) Antibodies 1–61 are from mice number 7 and 8. Antibodies 62–96 are from mice number 9.
(2) Response units by Mabs using biacore chip with attached sHuEPOR.
(3) Competition on BIACORE was to anti sHuEPOR Mab 1G2. sHuEPOR bound to a sensor chip was incubated with 1G2 then effect on Mab binding compared to binding to EPOR not pre-incubated with 1G2 was determined. Antibodies whose binding was completely blocked (80–100%) are A. Antibodies whose binding was blocked 50–80% are C. Antibodies whose binding was blocked less than 50% are B.
(4) Values for antibodies that gave cells a mean fluorescence greater than the control (12.73) are shown "—" indicates antibodies with a mean fluorescence less that or equal to control.
(5) Inhibition of 3H uptake by UT7-EPO cells. 30 munits of EPO and varying amounts of antibody were incubated with cells. After an overnight incubation cells were pulse labeled with 3H thymidine and the amount of counts taken up were determined. A positive response was defined as one that had a progressive decrease with increasing amounts of antibody
(6) Stimulation of 3H uptake by UT7-EPO cells. Varying amounts of antibody were incubated with cells. After an overnight incubation, cells were pulse labeled with 3H thymidine and the amount of counts taken up were determined. A positive response was defined as one that had a progressive increase in incorporation with increasing amounts of antibody.
(7) Inhibition was at concentrations higher than required to activate.

B. Epitope Competition Analysis

The sensor chip which was immobilized with sHuEPOR could be saturated by an injection of 65 μl of hybridoma supernatant 1G2. 1G2 is a monoclonal antibody raised to sHuEPOR using procedures described in Example 3. Each analysis cycle included injections of 20 ul of the hybridoma supernatant with and without one epitope being saturated by the injection of 65 ul of 1G2. The ratio of the binding signal in RU of 20 μl injection after 1G2 saturation versus the binding signal in RU of 20 μl injection alone is defined as % blocking by 1G2. Those antibodies with 80–100% blocking are assigned as group A, those with less than 50% blocking as group B, and those with 50–80% blocking as group C. The results are shown in Table 1.

C. Antibody Binding to d40EPOR on Transfected CHO Cells by Fluorescence-Activated Cell Sorting (FACS) Analysis Hybridoma supernatants raised against EPOR were tested for binding to EPO receptor on the surface of pDSRαEPORd40 transfected CHO cells by FACS analysis. CHO cells transfected with DNA encoding d40 EPO receptor were constructed as described in Example 1. CHO/EPOR cells were scraped from tissue culture dishes and resuspended as single cells in a solution of PBS/0.5% BSA and were then distributed into a 96 well round-bottom plate at approximately $3 \times 10^5$/well. The plate was then placed in the centrifuge at 1000× g for 5 min. After centrifugation, the PBS/BSA supernatant was removed and each of the pelleted cells were resuspended in either a control media or in one of the EPOR hybridoma supernatants. The cells were incubated at 4° C. for 1 hour. After the incubation, cells were washed with PBS/BSA and then resuspended in a solution of fluorescine isothiocyanate (FITC) labelled Goat anti Mouse monoclonal antibody (Southern Biotech, Birmingham Ala.). The cells were incubated again at 40° C. for 1 hour, washed and analyzed by FACS. Of the 96 supernatants tested, five had a mean cell fluorescence greater than control media (see Table 1). Mab 71 gave the highest level of fluoresence followed by Mabs 74, 58, 73 and 87. No other supernatants tested exhibited fluorescence above control values.

EXAMPLE 5

Purification of Anti-EPOR Antibodies and Fab Fragments

A. Ascites Production

Balb/c mice (Charles Rivers Laboratories, Wilmington, Mass.), greater that 5 weeks of age were primed with 2, 4, 10, 14-tetramethyl-pentadecane (Pristane; Sigma, St. Louis, Mo.) 7 to 10 days prior to injection of cell lines. Each mouse received a single intraperitoneal injection of 0.5 ml; 10 to 20 animals were injected for each cell line for which ascites fluid was to be prepared.

Hybridoma lines grown in complete medium until confluency was attained, were washed once with D-PBS then counted using a Neubauer Hemacytometer. Each mouse was then intraperitoneally injected with $10^7$ cells, and maintained on Rodent Lab Chow and water ad libitum until ascites fluid developed. Mice were monitored for maximum ascites formation, sacrificed under $CO_2$, and tapped for fluid collection using an 18G needle inserted into the fluid-filled cavity. The fluid was clarified by centrifugation at 225× g for 15 min or for 3 minutes in a microcentrifuge (Eppendorf). Four ml aliquots were then stored at −20° C. until purified by Protein-A column chromatography.

B. Protein-A Purification of Monoclonal Antibodies: Immunoglobulin from 4 ml of ascites fluid or 10 ml of hybridoma conditioned medium was purified by Protein-A column chromatography. The Bio-Rad Monoclonal Antibody Purification System II (MAPS II; Blo-Rad Laboratories; Richmond, CA) was used. Briefly, 5 ml of Affi-gel AFFI-GEL Protein-A suspension was settled into a 1×10 cm disposable glass column. The Protein-A gel was washed with approximately 30 ml of D-PBS then prepared by running 20 ml of Binding Buffer (MAPS II Binding Buffer; Bio-Rad) through the column. Ascites fluid or conditioned medium diluted 1:1 with binding buffer was then added to the top of the column and allowed to flow through. After binding of immunoglobulin to Protein-A, the unbound fraction was discarded. The column was next rinsed of unbound protein with 30 ml of binding buffer to yield an absorbance at 280 nm of less than 0.01. The immunoglobulin-containing fraction was then eluted with Bio-Rad Elution buffer, approximately 30 ml. This fraction was buffer-exchanged overnight at 40° C. by dialysis against 4 liters D-PBS. The resulting PBS-equilibrated immunoglobulin was concentrated by centrifugation at 1700 x g in CENTRICON® Concentrator units (Amicon Inc., Beverly, MA).

C. Fractionation of the Antibody-Binding Domain

Protein-A purified immunoglobulin was further fractionated into its 2 component parts, the crystalizable fraction (Fc) and the antibody-binding fraction (Fab), using a Pierce ImmunoPure Fab Preparation kit (Pierce Chemical Company, Rockford, Ill.). The protein-A purified immunoglobulin was dialyzed into 20 mM phosphate/10 mM EDTA buffer at pH 7.0, then concentrated to approximately 20 mg/ml. Ten mg of immunoglobulin was fractionated. Immobilized papain gel was rinsed twice with digestion buffer containing 42 mg cysteine in 12 ml phosphate buffer as supplied. The immunoglobulin sample was then added to the gel and incubated at 37° C., on a rotating shaker, overnight. The solublized Fab was separated from the Fc and undigested immunoglobulin by protein-A purification; unbound fraction was collected here as the Fab sample. This unbound portion was dialyzed overnight against 4 liters D-PBS at 4° C., and concentrated as before.

EXAMPLE 6

Mapping of Mab 71 Epitope on EPOR

Overlapping synthetic peptides 17 to 30 amino acids in length were made that spanned residues 1 to 224 of the human EPO receptor, where residue 1 is proline and residue 224 is aspartic acid. The ten different peptides overlapped by six amino acids at both ends. The sequences of the peptides and their location within the human EPO-R amino acid sequence are as follows:

```
SE-1  PPPNLPDPKFESKAALLAARGPEELCFTE
      (residuses 1-30) (SEQ. ID NO:4)

SE-2A LLCFTERLEDLVCFWEEA
      (residuses 25-42) (SEQ. ID NO:5)

SE-2B CFWEEAASAGcGPGNYSF
      (residuses 37-54) (SEQ. ID NO:6)

SE-3  PGNYSFSYQLEDEPWKLCRLHQAPTARGAV
      (residuses 49-78) (SEQ. ID NO:7)

SE-4  TARGAVRFWCSLPTADTSSFVPLELRVTAA
      (residuses 73-102) (SEQ. ID NO:8)

SE-5  LRVTAASGAPRYHRVIHINEVVLLDAPVGL
      (residuses 97-126) (SEQ. ID NO:9)

SE-6  DAPVGLVARLADESGHVVLRVLPPPETPMT
      (residuses 121-150) (SEQ. ID NO:10)

SE-7  PETPMTSHIRYEVDVSAGNGAGSVQRVEIL
      (residuses 145-174) (SEQ. ID NO:11)

SE-8  QRVEILEGRTECVLSNLRGRTRYTFAVRAR
      (residuses 169-198) (SEQ. ID NO:12)

SE-9  FAVRARMEAPSFGGFWSAWSEPVSLLTPSDLD
      (residuses 193-224) (SEQ. ID NO:13)
```

Figure 1:
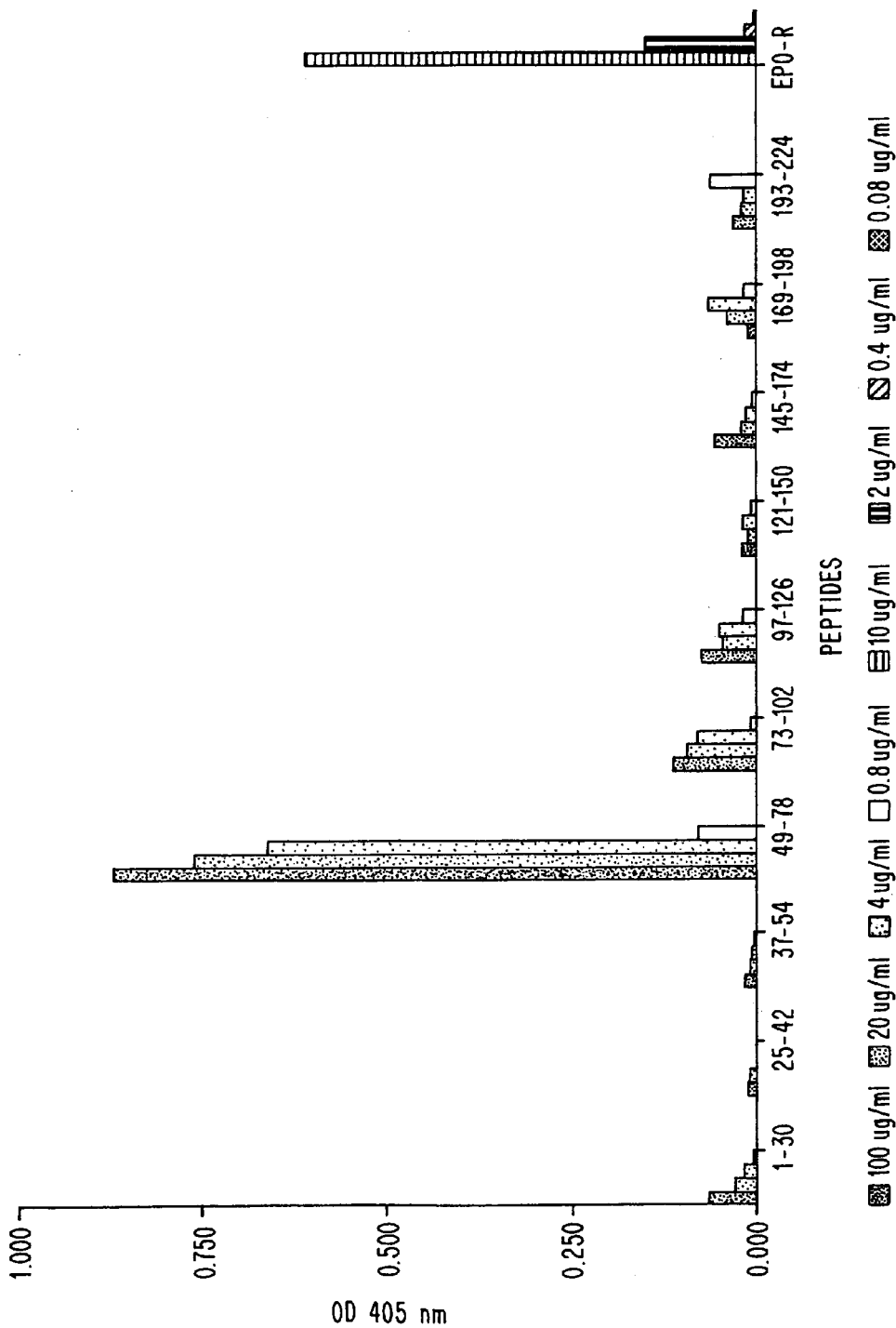
FIG. 1 shows the results of an ELISA assay that measured the binding to the indicated concentrations of synthetic peptides by Mab 71. The peptides correspond to the indicated amino acid residues of human EPO receptor. Residue 1 is the amino terminal proline found in secreted EPOR upon cleavage of the leader sequence.

Polystyrene wells (Costar, Cambridge, Mass.) were coated with the above EPO-R peptides at concentrations of 100 µg/ml, 20 µ/ml and 0.8 µg/ml respectively in carbonoate-biocarbonate buffer (0.015M $Na_2CO_3$, 0.035M $NaHCO_3$, pH 9.2). The plate was incubated at room temperature (RT) for 2 hours then overnight at 4° C. Soluble HuEPOR was coated at concentrations of 10µg/ml, 2µg/ml, 0.4 µg/ml and 0.08ug/ml as positive controls under the same conditions. After blocking with 5% BSA in PBS at RT for 30 minutes, the plate was incubated with Mab 71 purified as described in Example 5 at a concentration of 5µg/ml in 1% BSA at RT for 2 hours. After washing with washing buffer (Kirkegard and Perry Labs, Inc.) the plate was incubated with 1:1000 dilution of Goat anti-mouse IgG conjugated with horse Radish peroxidase (Boehringer Mannheim) for one hour at RT. The plate was washed and developed with ABTS (Kirkegard and Perry Labs, Inc.) substrate solution. Colorimetry was conducted at 405 nm. The results of Mab binding to the synthetic peptides are shown in FIG. 1 and indicate that Mab 71 binds significant amounts of peptide SE-3 (amino acid residues 49 to 78 inclusive of human EPO-R) compared to the other peptides tested. This indicates that Mab/1 binds to a region of the human EPO-R containing or overlapping residues 49 to 78.

EXAMPLE 7

Activity of Anti-EPOR Antibodies in Cell Proliferation Assays

Antibodies in conditioned medium prepared as described above were assayed for their ability to stimulate uptake of 3H-thymidine by UT7-EPO cells (Komatsu et al., supra). UT7-EPO cells are responsive to EPO and express human EPO receptors on their cell surface. UT7-EPO cells were grown in Growth medium (1× Iscove's Modified Dulbecco's Medium with L-glutamine, 25 mM HEPES buffer, and 3024 mg/L sodium bicarbonate, but without either alpha-thioglycerol or beta-mercaptoethanol (GIBCO)/10% v/v Fetal Bovine Serum/1% v/v L-glutamine-Penicillin-Streptomycin solution (Irvine Scientific)/1 Unit/ml rHuEPO ) to approximately $3\times10^5$ cells/ml. Cells were collected by centrifugation (approx. 500× G) washed twice with phosphate buffered saline and resuspended at 5×10⁴ cells/ml in Assay medium (1× RPMI Medium 1640 without L-glutamine (Gibco)/1% L-glutamine/4% fetal bovine serum). Test samples or EPO standard (rHuEPO), 100 µL diluted in assay medium at least 5-fold, were added to wells in a 96 well microtiter plate. 50 µL cells were then added (5000 cells/well) and plates were incubated in a humidified incubator at 37° C. and 5% $CO_2$. After 72 hours, 50 µL methyl-³H-Thymidine (1 mCi/ml; 20 Ci/mMole) diluted 1:100 in assay medium was added. Cells were incubated for an additional 4 hours at 37° C. and 5% $CO_2$. Labeled cells were harvested onto glass fiber filtermats using a PHD cell harvester(Cambridge Technology Inc.) and deionized water as a washing solution. Filters were rinsed a final time with 2 propanol then dried and counted in a Beckman Model LS6000IC scintillation counter.

Conditioned medium from tissue culture plates containing antiEPOR Mabs were tested for their ability to stimulate proliferation as described above. Samples at several dilutions were tested. Positive responses were defined as those that stimulated thymidine uptake at least 2-fold over background levels and also resulted in decreasing stimulation as the samples were diluted. As shown in Table 1, two samples out of 24 tested gave a positive response (Mabs 71 and 73). Four samples may have a weak stimulatory activity (? in Table 1). The remaining samples did not give a significant increase over background. A polyclonal serum from the mouse used to generate monoclonals also stimulated thymidine uptake. This suggests that the polyclonal antibody in this serum was also capable of stimulating proliferation of UT7-EPO cells.

The supernatants were also tested for their ability to inhibit EPO-induced stimulation of thymidine uptake by UT7-EPO cells. Cells were incubated with 25 munits/ml rHuEPO and varying amounts of antibody containing conditioned medium. Thymidine uptake was measured as described above. The results are shown in Table 1. Most antibodies did not significantly differ from control medium. Of the antibodies showing inhibition of thymidine uptake, two samples (Mabs 58 and 73) showed definite inhibition while three samples (Mabs 65, 88 and 89) showed possible inhibition. Mab 73 inhibited at the highest doses but at lower doses it stimulated thymidine uptake over control values.

EXAMPLE 8

Activation of EPOR by Anti-EPOR Antibodies and Fragments

A. UT7-EPO Proliferation Assay Mabs 71 and 73 were purified as described in Example 5. Proliferative activity was determined with UT7-EPO thymidine uptake assays described in Example 7. Both Mabs 71 and 73 stimulated uptake by UT7-EPO cells in a dose dependent manner as did rHuEPO (see FIG. 2). Activity was reduced at high doses of Mab 71. Peaks in stimulatory activity were observed at doses of 1–2 µ/ml for Mab 71 and >100 µg/ml for Mab 73. A nonneutralizing control antibody (AntiEPO Mab F12) did not stimulate which suggests that the stimulation is specific for EPO receptor antibodies.

B. EPO Cold Displacement Assays.

Antibodies to the EPO receptor may bind to the same region as EPO binds. To test this possibility, cold displacement assays were performed using OCIM1 cells. OCIM1 cells are from human origin and known to contain EPO receptors on their cell surface (Broudy et al. Proc. Nat. Acad. Sci. USA 85, 6517 (1988)). Cells were grown in OCIM1 growth medium (Iscove's modified Dulbecco medium (IMDM)/10% fetal bovine serum/1% pen-strep-fungisone) to approximately 2–5×10⁵ cells/ml. Cells were collected by centrifugation, washed two times in binding buffer (RPMI 1640/1% BSA/25mM HEPES pH 7.3) then resuspended in binding buffer containing 0.1% azide and 10 µ/ml cytochalisin B at 1–2×10⁷ cells/ml. Cells (100 µL) in 96 well tissue culture plates were then incubated with 10 µL sample and 10 µL ¹²⁵I-EPO (Amersham high specific activity; 3000 Ci/mMole, 2 µCi/ml) in a 37° humidified tissue culture incubator. After 3 hours cells were centrifuged through phthalate oil (60:40 (v/v) dibutyl/dinonyl phthalate) in titer tubes. The tubes containing cells were quick frozen in a dry ice-ethanol bath and the cell pellet was clipped and then counted in a LKB 1277 gammamaster automatic gamma counter.

Figure 3:
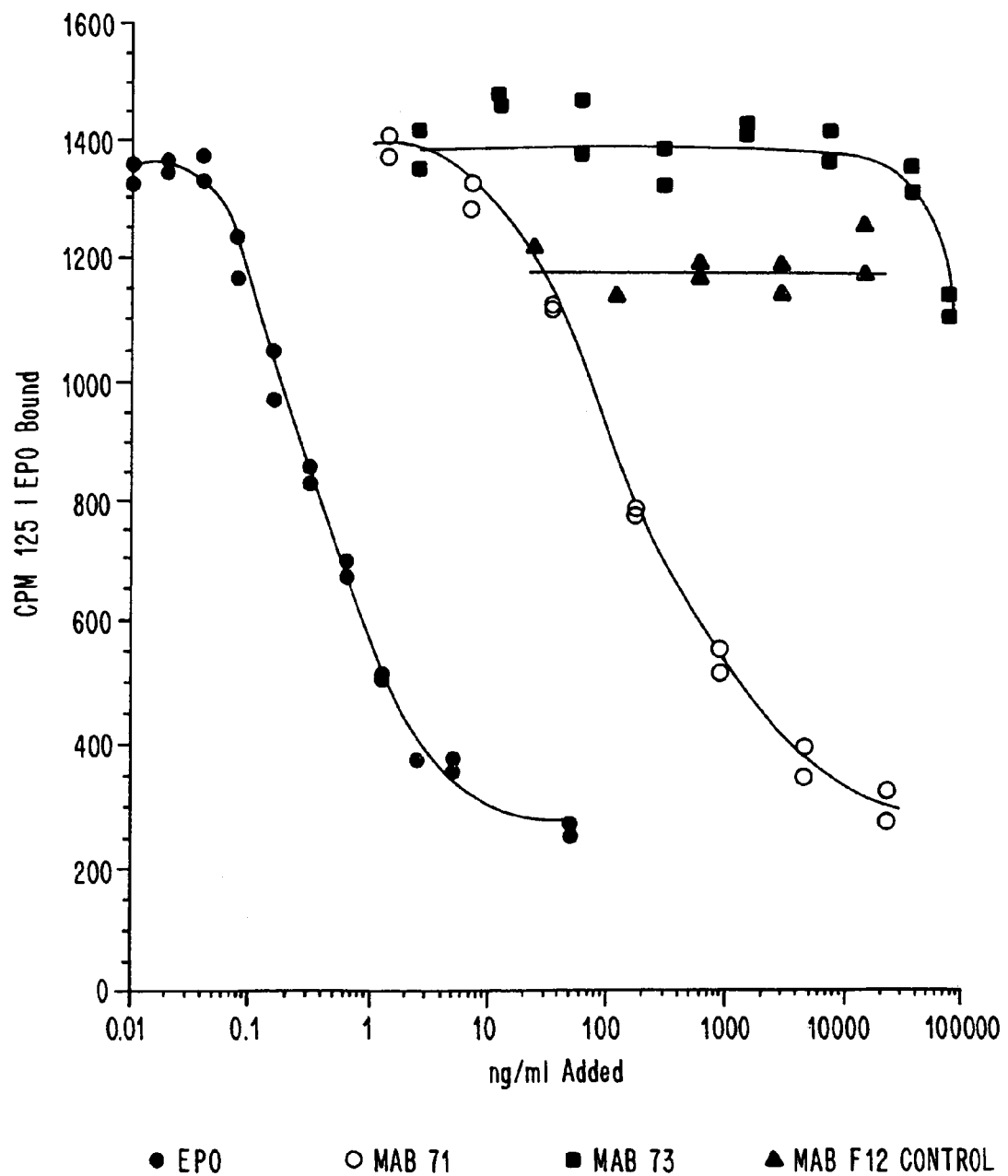
FIG. 3 shows the effect of varying amounts of rHuEPO protein, Mab 71, Mab 73 or a non neutralizing control Mab directed against EPO (Mab F12) on inhibition of $^{125}$I EPO binding to EPO receptors on the surface of OCIM1 cells.

FIG. 3 shows the results of the cold displacement experiment. Increasing amounts of ¹²⁵I-EPO were displaced from EPO receptors on cells as the amount of added unlabeled rHuEPO was increased. In a similar manner, Mab 71 purified as described in Example 5 also displaced increasing amounts of ¹²⁵I-EPO with increasing amounts of antibody. In this case, approximately 4,000 fold more Mab 71 was needed than rHuEPO to displace equivalent amounts of ¹²⁵I-EPO. In contrast Mab 73 showed indications of displacement at the highest doses but a nonneutralizing anti rHuEPO Mab (F12) did not significantly displace. These results indicate that Mab F12 did not interfere with binding of EPO to its receptor but Mab 71 and 73 do. This result also indicates that Mab 71 binds to the EPO receptor and activates it by binding at or close to the EPO binding site.

C. Comparison of activities of Mab 71 and Fab 71

Figure 4:
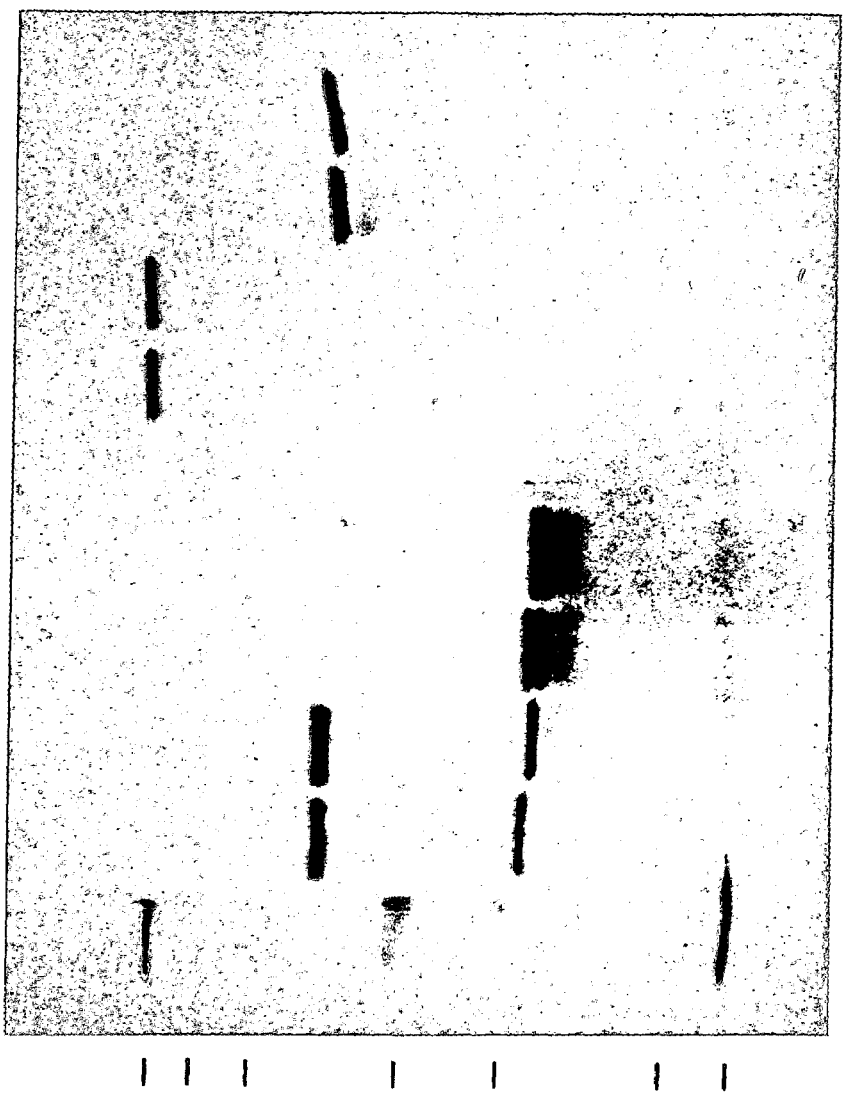
FIG. 4 shows a coomassie stained SDS gel of purified preparations of monoclonal antibodies 71 and 73 as well as monoclonal antibody fragments (Fabs) derived from Mabs 71 and 73. Samples were run under either reducing (plus 2-mercaptoethanol) or nonreducing (minus 2-mercaptoethanol) conditions.

EPO receptor fragments of Mab 71 were prepared as described in Example 5. The preparations were characterized by SDS gel electrophoresis (Laemmli et al. Nature 227, 680 (1970) as shown in FIG. 4. Samples were boiled in 2% SDS containing sample buffer with or without 0.7M 2-mercaptoethanol, to distinguish reduced (2-mercaptoethanol) from nonreduced (no 2-mercaptoethanol) proteins, then run on 12.5% acrylamide SDS gels. The gels were stained with coomassie blue to visualize the proteins. The sizes of the proteins were estimated by comparing their mobilities to the mobilities of protein standards. Mabs 71 and 73 separated into light and heavy chains when run under reducing conditions. The heavy chains were approximately 52 KDa. The light chain for 73 was slightly smaller (28 KDa) than for Mab 71 (28.5 KDa). The Fab fragments also had two chains: 28.3 and 27.3 KDa for Fab 71 and 27.5 and 26.5 KDa for Fab 73. When these Fab fragments were run under non reducing conditions, the sizes of Fabs 71 and 73 were approximately 48 and 47 KDa respectively. This indicates that the Fab fragments are monovalent, the complex has one each of the light and heavy chains. In contrast the mobilities on nonreducing SDS gels for Mabs 71 and 73 indicated that their sizes were approximately 200 KDa. This indicates that these Mabs are bivalent, there are two each of the heavy and light chains.

To see if monovalent Fab 71 fragments would activate the EPO receptor, Mab 71 and the Fab 71 fragment were incubated with UT7-EPO cells and thymidine uptake was measured as described in Example 7. As shown in FIG. 5, both rHuEPO and Mab 71 stimulated thymidine uptake. However the monovalent Fab 71 fragment did not. A control monoclonal antibody raised against an unrelated receptor (Her2/neu) also did not stimulate thymidine uptake. This indicates that the antibodies must be bivalent in order to activate the receptor.

D. Stimulation of Thymidine Uptake by Mab 71 and Fab 71 in the Presence of rHuEPO.

Figure 6:
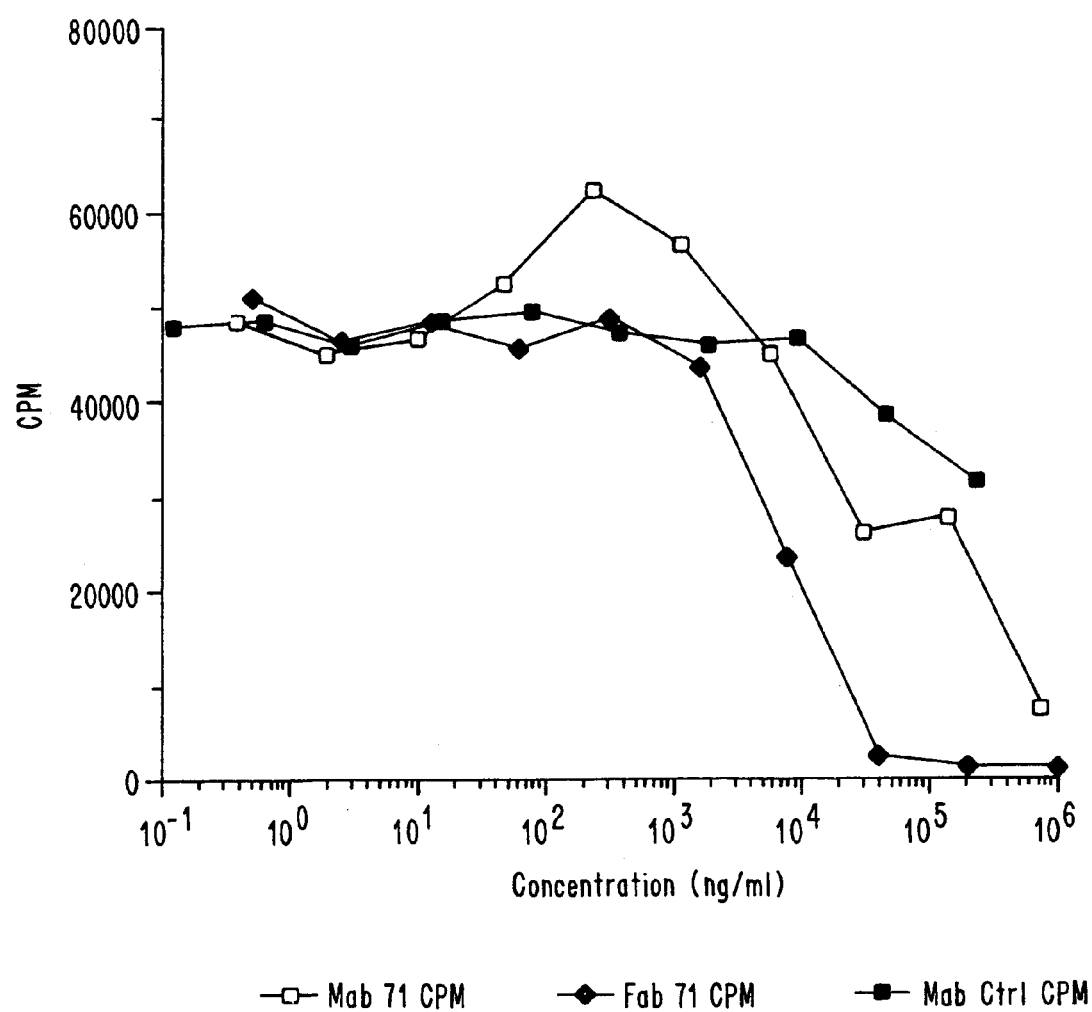
FIG. 6 shows the effect of varying amounts of purified Mab 71 or Fab 71 on $^3$H thymidine uptake of UT7-EPO cells to which are also added 30 munits/ml of recombinant human EPO (rHuEPO).

The fact that Mab 71 inhibits binding of EPO to EPO receptors suggested that the antibody may not activate the EPO receptor in the presence of EPO. To test this possibility UT7-EPO cells were incubated with 30 munits/ml rHuEPO and varying amounts of purified Mab 71, Fab 71 or Mab control (raised against Her2/neu). Thymidine uptake was measured as described above. As shown in FIG. 6 Both Mab 71 and Fab 71 inhibited thymidine uptake at high doses. However at doses between approximately 30 and 3000 μ/ml, Mab 71 stimulated thymidine uptake above levels stimulated by rHuEPO alone. Fab 71 and control antibodies did not have this effect. This indicates that Mab 71 and rHuEPO can have an additive effect in EPO receptor activation.

EXAMPLE 9

Stimulation of Erythroid Colony Formation by Anti-EPOR Antibodies

To see if purified Mab 71 would stimulate formation of erythroid cells from precursors in peripheral blood a BFUe assay was done. To purify erythroid cell precursors, normal human donors were lymphopheresed according to standard protocol. The lymphopheresed cells (250 ml) were washed with 250 ml Hank's Balanced Salt Solution (HBSS). The cells were resuspended in HBSS and separated by density centrifugation over a gradient(Ficoll-paque) for 30 min at 500× g. The low density cells(LD) were collected from the gradient and washed with 500 ml HBSS and resuspended in PBS supplemented with 0.5% bovine serum albumin and 5 mM EDTA at a concentration of $5 \times 10^8$ cells/ml. The LD cells were then further purified using a CD34 progenitor Cell Isolation Kit (QBend/10) made by Miltenyi Biotech GmbH. In brief cells were tagged with an anti CD34 monoclonal antibody they were then bound to magnetic microspheres according to protocol. The tagged cells were next passed through pre-filled MiniMacs separation columns, the columns were washed and the CD34+ cells were then eluted from the column. This process was repeated once more to achieve a higher purity of CD34+ cells. The in vitro assay was done on the purified CD34+cells as described by Iscove et. al. (J. Cell. Physiol 83, 309 (1974)) with the following modifications. The culture medium was obtained from Gibco BRL (Human bone marrow stem cell proliferation kit; Grand Island, N.Y.). To plate out duplicate 1 ml samples on 35×100 mm tissue culture plates, an excess of 3 ml was prepared in 17×100 sterile polystyrene tubes. Each tube received 2.5 ml Stem Cell Growth medium, 0.1 ml CD34+ cells (resuspended at 90,000 cells/ml) 0.015 ml Stem Cell Factor (20 μ/ml), and a combination of sample and Stem Cell Dilution medium equaling 0.385 ml. The tubes were vortexed and allowed to settle to allow bubbles to rise. The contents were then aliquoted using a 3 ml syringe with a 17×1-½ needle. The plates were incubated at 37° C. and 10% $CO_2$ in a humidified tissue culture incubator. Erythroid colonies (orange to red in color) were scored after 21 days. No erythroid colonies were seen in plates lacking EPO or Mab 71. rHuEPO (30 mUnits/plate) gave an excess of 400 colonies per plate. Mab 71 also produced erythroid colonies. Peak activity was seen at 2–6 μ/ml. This result indicates that Mab 71 stimulates formation of erythroid colonies.

Figure 8:
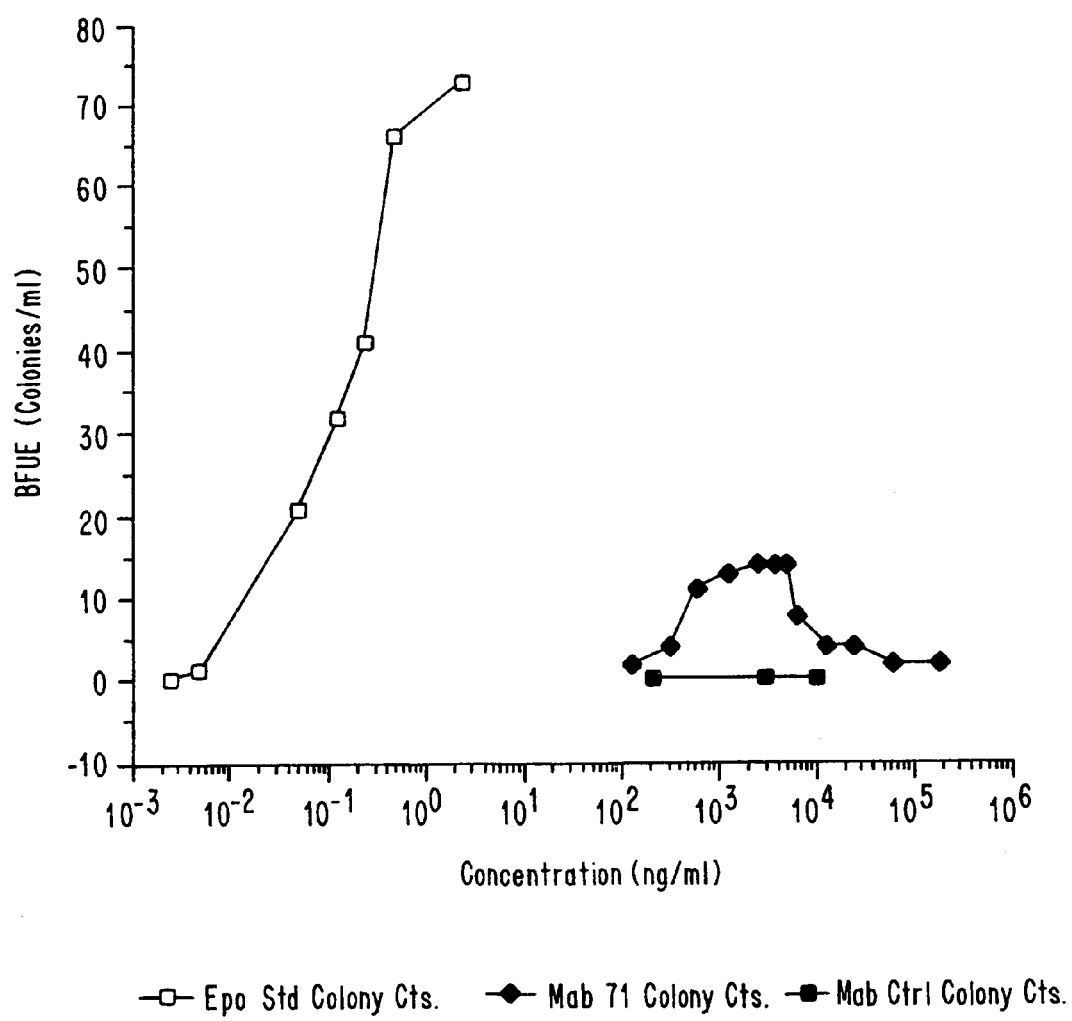
FIG. 8 shows the effect of varying amounts of rHuEPO, Mab 71 and a control monoclonal antibody raised to Her2/neu on the formation of erythroid colonies from erythroid precursors when grown under serum free growth conditions in soft agar.

The activity of purified Mab 71 was also tested for the ability to form erythroid colonies using serum free growth conditions in methylcellulose. CD34+cells were isolated as described above and incubated using the serum free growth medium described in co-pending and co-owned U.S. Ser. No. 08/079,719, hereby incorporated by reference, with the following modifications. The assay tubes were set up without using extracellular matrix molecules, hydrocortisone, and the growth factors EGF, FGF, and PDGF. As described above 3 mL of sample was prepared to plate out duplicate 1 mL samples on plates. Each tube received 0.030 ml each of 100× Stock Solutions (2-Mercaptoethanol, nucleosides, cholesterol, Sodium-Pyruvate, Hu-Transferrin, lipids, Hu-Insulin), 0.4 ml deionized BSA (15%), 0.015 ml SCF (20 ug/ml), 0.1 ml CD34+ cells (resuspended at 300,000 cells/ml), 1.080ml methylcellulose (2.3%), and a combination of sample and IMDM equaling 1.195 ml where the sample did not exceed 150 μl. The plates were then incubated as described above and colonies were scored after 21 days. Erythroid colonies were observed when grown in the presence of EPO or Mab 71 but not under conditions lacking these two factors. An example of the erythroid colony types seen is shown in FIG. 7. Colonies incubated with 25 munits of rHuEPO looked similar to those grown with 2.1 μ/ml of purified Mab 71. Higher doses of rHuEPO gave larger colonies. A dose response curve is shown in FIG. 8. Mab 71 had a peak in activity at doses between 1 and 5 μg/ml. Lower and higher doses resulted in fewer erythroid colonies. A control monoclonal antibody raised to Her2/Neu did not produce any colonies over this dose range. This result indicates that the Mab 71 will stimulate the formation of erythroid colonies from erythroid precursors and that there is not an additional requirement for serum. Thus Mab 71 can stimulate differentiation of erythroid precursors into erythroid cells.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A monoclonal antibody or bivalent fragment thereof which binds to an erythropoietin receptor, wherein the antibody or bivalent fragment thereof binds to a peptide consisting of the amino acid sequence as set forth in SEQ ID NO: 7, and wherein the antibody or bivalent fragment thereof has one or more activities selected from: (i) stimulation of proliferation of erythropoietin-responsive cells, (ii) stimulation of uptake of $^3$H-thymidine into erythropoietin-responsive cells in the absence of erythropoietin, and (iii) stimulation of the formation of erythroid colonies from erythroid precursors.

2. The antibody or bivalent fragment thereof of claim 1 which stimulates the proliferation of erythropoietin-responsive cells.

3. The antibody or bivafent fragment thereof of claim 1 which stimulates the uptake of 3H-thymidine into erythropoietin-responsive cells in the absence of erythropoietin.

4. The antibody or bivalent fragment thereof of claim 1 which stimulates the formation of erythroid colonies from erythroid precursors.

5. The antibody or biva Went fragment thereof of claim 1, wherein the erythropoietin receptor is a mammalian erythropoietin receptor.

6. The antibody or bivalent fragment thereof of claim 1, wherein the erythropoietin receptor is a human erythropoiehin receptor.

7. The antibody or bivalent fragment thereof of claim 1 which is a human antibody.

8. A detectably labeled monoclonal antibody or bivalent fragment thereat said detect ably labeled monoclonal antibody or bivalent fragment thereof comprising the monoclonal antibody or bivalent fragment thereof of claim 1, and further comprising a detectable label.

9. A monocional antibody or bivalent fragment thereof which competes with a monoclonal antibody produced by hybridoma cell line ATCC No. HB 11689 or ATCC No. HB 11690 for binding to an erythropoietin receptor, and wherein the antibody or bivalent fragment thereof has one or more activities selected from (i) stimulation of proliferation of erythropoietin-responslve cells, (ii) stimulation of uptake of 3H-thymidine into erythropoietin-responsive cells in the absence of erythropoietin, and (iii) stimulation of the formation of erythroid colonies from erythroid precursors.

10. The antibody or bivalent fragment thereof of claim 9 which stimulates the proliferation of erythropoieun-responsive cells.

11. The antibody or bivalent fragment thereof of claim 9 which stimulates the uptake of 3H-thymidine into erythropoietin-responsive cells in the absence of erythropoietin.

12. The antibody or bivalent fragment thereof of claim 9 which stimulates the formation of erythroid colonies from erythroid precursors.

13. The antibody or bivalent fragment thereof of claim 9 which competes with a monoclonal antibody produced by hybridoma cell line ATGC No. HB 11689 for binding to the erythropoietin receptor.

14. The antibody or bivalent fragment thereof of claim 9, wherein the erythropoietin receptor is a mammalian erythropoietin receptor.

15. The antibody or bivalent fragment thereof of claim 9, wherein the erythropoietin receptor is a human erythropoietin receptor.

16. The antibody or bivalent fragment thereof of claim 9 which is a human antibody.

17. A detectably labeled monoclonal antibody or bivalent fragment thereot said detectably labeled monoclonal antibody or bivalent fragment thereof comprising the monoclonal anti body or bivalent fragment thereof of claim 9, and further comprising a deteotabre label.

* * * * *

UNITED STATES PATENT AND TRADEMARK OFFICE
CERTIFICATE OF CORRECTION

PATENT NO. : 7,081,523 B2
APPLICATION NO. : 10/364276
DATED : July 25, 2006
INVENTOR(S) : Steven Elliott It is certified that error appears in the above-identified patent and that said Letters Patent is hereby corrected as shown below:

In Claim 3, col. 29, line 52, "bivafent" should read --bivalent--;

In Claim 3, col. 29, line 53, "3H-thymidine" should read --$^3$H-thymidine--.

In Claim 5, col. 29, line 58, "biva Went" should read --bivalent--.

In Claim 6, col. 29, lines 62-63, "erythropoiehin" should read --erythropoietin--.

In Claim 8, col. 29, line 67, "thereat" should read --thereof,--;

In Claim 8, col. 29, line 67, "detect ably" should read --detectably--.

In Claim 9, col. 30, line 40, "monocional" should read --monoclonal--;

In Claim 9, col. 30, line 47, "3H-thymidine" should read --$^3$H-thymidine--.

In Claim 10, col. 30, lines 51-52, "erythropoieun-responsive" should read --erythropoietin-responsive--.

In Claim 11, col. 30, line 55, "3H-thymidine" should read --$^3$H-thymidine--.

In Claim 13, col. 30, line 63, "ATGC" should read --ATCC--.

In Claim 17, col. 31, line 7, "thereot" should read --thereof,--;

In Claim 17, col. 32, line 2, "anti body" should read --antibody--;

In Claim 17, col. 32, line 3, "deteotabre" should read --detectable--.

Col. 1, line 49, "Eur. J. Biochem. 1, 271" should read --Eur. J. Biochem. 194, 271--.

Col. 7, line 11, "example 3" should read --Example 3--.

Col. 7, lines 46-57, delete the text beginning with "The antibodies of the present invention" to and ending with "allow for detection. The".

Col. 9, lines 20 and 22, "Sall" should read --SalI--.

UNITED STATES PATENT AND TRADEMARK OFFICE
CERTIFICATE OF CORRECTION

PATENT NO.         : 7,081,523 B2
APPLICATION NO.    : 10/364276
DATED              : July 25, 2006
INVENTOR(S)        : Steven Elliott It is certified that error appears in the above-identified patent and that said Letters Patent is hereby corrected as shown below:

Col. 10, line 13, "H2O" should read --$H_2O$--.

Col. 11, line 13, "1.2 Mto" should read --1.2 M to--.

Col. 19, line 18, "Blo-Rad Laboratories" should read --Bio-Rad Laboratories--.

Col. 21, line 50, insert a line break between "Proliferation Assay" and "Mabs 71".

Col. 23, line 45, "CD34+cells" should read --CD34+ cells--.

Col. 24, line 15, "CD34+cells" should read --CD34+ cells--.

Signed and Sealed this

Nineteenth Day of December, 2006

JON W. DUDAS
*Director of the United States Patent and Trademark Office*

SEQUENCE LISTING

<160> NUMBER OF SEQ ID NOS: 13

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: PCR primer

<400> SEQUENCE: 1
ctccaagctt gccgtcacca tggaccacct cggggcgtcc ct        42

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 2
caggtctaga ttactaggga tccaggtcgc taggc        35

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 3
aggtcgacta ctagtagtca gttgaga        27

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: synthetic peptide

<400> SEQUENCE: 4

Pro Pro Pro Asn Leu Pro Asp Pro Lys Phe Glu Ser Lys Ala Ala Leu
 1               5                  10                  15
Leu Ala Ala Arg Gly Pro Glu Glu Leu Cys Phe Thr Glu
            20                  25

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: synthetic peptide

<400> SEQUENCE: 5

Leu Leu Cys Phe Thr Glu Arg Leu Glu Asp Leu Val Cys Phe Trp Glu
 1               5                  10                  15
Glu Ala

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence: synthetic peptide

<400> SEQUENCE: 6

Cys Phe Trp Glu Glu Ala Ala Ser Ala Gly Val Gly Pro Gly Asn Tyr
 1               5                  10                  15
Ser Phe

```
<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Pro Gly Asn Tyr Ser Phe Ser Tyr Gln Leu Glu Asp Glu Pro Trp Lys
  1               5                  10                  15

Leu Cys Arg Leu His Gln Ala Pro Thr Ala Arg Gly Ala Val
             20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Thr Ala Arg Gly Ala Val Arg Phe Trp Cys Ser Leu Pro Thr Ala Asp
  1               5                  10                  15

Thr Ser Ser Phe Val Pro Leu Glu Leu Arg Val Thr Ala Ala
             20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Leu Arg Val Thr Ala Ala Ser Gly Ala Pro Arg Tyr His Arg Val Ile
  1               5                  10                  15

His Ile Asn Glu Val Val Leu Leu Asp Ala Pro Val Gly Leu
             20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Asp Ala Pro Val Gly Leu Val Ala Arg Leu Ala Asp Glu Ser Gly His
  1               5                  10                  15

Val Val Leu Arg Val Leu Pro Pro Glu Thr Pro Met Thr
             20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 11

Pro Glu Thr Pro Met Thr Ser His Ile Arg Tyr Glu Val Asp Val Ser
```

-continued

```
                1               5              10              15
Ala Gly Asn Gly Ala Gly Ser Val Gln Arg Val Glu Ile Leu
                20                              25                              30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Gln Arg Val Glu Ile Leu Glu Gly Arg Thr Glu Cys Val Leu Ser Asn
 1               5                              10                              15

Leu Arg Gly Arg Thr Arg Tyr Thr Phe Ala Val Arg Ala Arg
                20                              25                              30

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Phe Ala Val Arg Ala Arg Met Glu Ala Pro Ser Phe Gly Gly Phe Trp
 1               5                              10                              15

Ser Ala Trp Ser Glu Pro Val Ser Leu Leu Thr Pro Ser Asp Leu Asp
                20                              25                              30
```